United States Patent [19]
Takeda et al.

[11] Patent Number: 5,936,726
[45] Date of Patent: Aug. 10, 1999

[54] INSPECTION METHOD, INSPECTION APPARATUS AND METHOD OF PRODUCTION OF SEMICONDUCTOR DEVICE USING THEM

[75] Inventors: Kazuo Takeda, Tokorozawa; Hidetsugu Ishida, Kodaira; Atsushi Hiraiwa, Higashi-murayama, all of Japan

[73] Assignee: Hitachi Ltd., Tokyo, Japan

[21] Appl. No.: 08/913,392

[22] PCT Filed: Mar. 10, 1996

[86] PCT No.: PCT/JP95/00398

§ 371 Date: Sep. 9, 1997

§ 102(e) Date: Sep. 9, 1997

[87] PCT Pub. No.: WO96/28721

PCT Pub. Date: Sep. 19, 1996

[51] Int. Cl.$^6$ ................................................ G01N 21/00
[52] U.S. Cl. ................................ 356/237.2; 356/237.3; 356/237.4; 356/237.5
[58] Field of Search ........................... 356/237–239, 356/237.1–237.6

[56] References Cited

U.S. PATENT DOCUMENTS 4,893,932  1/1990  Knollenberg ........................... 356/237

FOREIGN PATENT DOCUMENTS

| 62-73141 | 4/1987 | Japan . |
| 2-61540 | 3/1990 | Japan . |
| 5-264468 | 10/1993 | Japan . |
| 5-332913 | 12/1993 | Japan . |
| 5-340884 | 12/1993 | Japan . |

Primary Examiner—Robert H. Kim
Assistant Examiner—Amanda Merlino
Attorney, Agent, or Firm—Antonelli, Terry, Stout & Kraus, LLP

[57] ABSTRACT

An inspection method and apparatus for discriminating the foreign particles on the surface of a sample from the foreign particles or defects within the sample, and a semiconductor-device producing method using the inspection method and apparatus. The inspection apparatus includes a light source, a first optical system that causes the light from the source to be directed to the sample, a second optical system for condensing the light coming back from the sample, a polarizing prism for separating the condensed light into polarized components, and optical detectors, for detecting the polarized components. The two optical systems, are arranged for their optical axes to make an angle of 50° to 120° relative to each other. The foreign particles on the surface of the sample and the foreign particles or defects within the sample are respectively discriminated from each other as side scattered light and backward scattered light by utilizing the difference between the intensity ratios of the polarized light components.

17 Claims, 18 Drawing Sheets

NOTE: $\sigma(x)$: SCATTERING CROSS-SECTION AREA OF $SiO_2$ WITHIN SILICON RELATIVE TO RADIATED LIGHT (WAVELENGTH x nm)

INSPECTION METHOD, INSPECTION APPARATUS AND METHOD OF PRODUCTION OF SEMICONDUCTOR DEVICE USING THEM

TECHNICAL FIELD

The present invention generally relates to the inspection of foreign particles attached on the surface of an object and measurement of defects within the object, and particularly to an inspection method of and apparatus for detecting foreign particles attached on the surface of a silicon crystal and on the surface of an amorphous silicon thin film, and for measuring crystal defects such as oxygen precipitates in a silicon wafer, and foreign particles within an amorphous silicon thin film, to standard samples for the correction of this apparatus, and to a semiconductor production method using this method or apparatus.

BACKGROUND ART

Recently, the integration density of LSIs (Large Scale Integrated Circuits) has been increased, and caused the serious problem that the yield of satisfactory MOS (Metal Oxide Semiconductor) transistors which form devices, and the reliability are decreased due to the defective transistors. The defectiveness of MOS transistors will be caused due to, typically, breakdown of insulating gate oxide films and excessive leak current in junctions. The latter gives rise to the loss of information called poor refreshment in DRAM (Dynamic Random Access Memory). These causes for unsatisfactory MOS transistors are ascribed to not only the foreign particles on the surface of the silicon substrate in which devices are built up, but also crystal defects present in the region near the surface. The region near the surface of the silicon substrate is specifically in the range from the substrate surface to about 0.5 $\mu$m deep, and this region is a portion of the substrate that is converted into an oxide insulated layer (silicon oxide film) in the production process for devices such as LSIs or into a depletion layer when a metal thin film is deposited on the substrate surface. The crystal defects located within this portion form structural defects in the silicon oxide film, and causes insulation breakdown in the LSI operation. The defects in the depletion layer causes a large amount of leak current to occur. On the contrary, crystal defects located in the region deeper than the near-surface region, particularly, oxygen precipitates, have the effect (gettering effect) to catch metal ions mixed into the silicon substrate in various production processes, preventing the near-surface region of the substrate from being contaminated with metal.

Therefore, for the quality control of silicon substrates in which LSIs are formed, it is necessary to provide an inspection apparatus capable of not only detecting foreign particles on the substrate surface, but also selectively detecting crystal defects located in the near-surface region.

Moreover, when liquid crystal displays which are formed of thin film transistors (for example, amorphous silicon thin films) are produced under quality control, it is essential to detect the foreign particles on the surface of a transparent substrate on which thin films are formed, the foreign particles or defects present in the near-surface region, and the foreign particles which are mixed into the interior of the thin films in the thin film depositing process or which adhere to the substrate surface.

There is proposed an apparatus for detecting foreign particles or defects on or below the surface of a sample by irradiating S-polarized light and P-polarized light on the sample surface, as is disclosed in Japanese Patent Laid-open JP-A-63-12943 (or U.S. Pat. No. 4,893,932 associated therewith). This apparatus detects the foreign particles or defects located on the sample surface by utilizing the fact that the intensity distributions of the irradiation light scattered by the foreign particles and defects on the sample surface are different depending on the polarization direction. However, the specification disclosing the apparatus of the invention does not specifically describe any means for detecting the foreign particles or defects present on the lower side (namely, in the medium of which the refractive index is larger than that of air) of the sample surface.

As disclosed in Japanese Patent Laid-open JP-A-5-264468, another apparatus is proposed for irradiating on a tested object first light of a wavelength for extracting relatively more optical information of the object surface and second light of a wavelength for extracting relatively more optical information of the interior of the object, and observing the optical images scattered (scattered images) by the defects on the surface or within the interior of the object in association with the first wavelength and second wavelength. This apparatus determines if the defects are located on the surface or within the interior of the object by comparing the scattered images of first and second wavelengths, and also acquires the depth information of the defects within the interior of the object from the scattered image of the second wavelength. However, since the depth at which the defects are located within the interior of the object is detected by use of only the second wavelength light (the optical information by the first wavelength light is removed and the information of only the internal defects is extracted), the resolution of the depth detection is determined by the optical image forming performance. Thus, since the wavelength of the radiated light is about 1 $\mu$m, the defects in the near-surface region of the silicon substrate cannot be selectively detected. In addition, the above JP-A publication does not describe any means for solving the problem that the second wavelength light is attenuated in the interior of the object being tested.

Moreover, in Japanese Patent Laid-open JP-A-2-61540 disclosed is another defect inspecting apparatus capable of easily determining if foreign particles are located on the upper or lower side of the surface of a transparent, flat object (such as thin film or relatively thin transparent plate) and detects the sizes of the foreign particles. This apparatus radiates first and second light beams of different transmission factors on the object, and determines if the foreign particles are located on the incidence surface or the opposite side of the object by comparing the intensities of the scattered light signals. However, the above JP-A publication does not describe anything about the detection of the depth at which the defects are located within the interior of the object being inspected.

Before detecting the foreign particles on the surface of the sample and the foreign particles or crystal defects in the near-surface region, we need standard samples for correcting the detection sensitivity of measuring equipment and so on. A standard sample for detection of foreign particles on the surface, or standard particles, of which the refractive index and size are known, deposited on a substrate surface, is disclosed in Japanese patent Laid-open JP-A-5-340884. In addition, a standard sample of particle images reduced and transferred onto a transparent substrate is disclosed in Japanese Patent Laid-open JP-A-5-332913. However, there is no document which describes a standard sample for detecting the defects located in the near-surface region of the sample, or located within the sample at a depth that is shorter than the wavelength of the irradiation light.

DISCLOSURE OF THE INVENTION

The apparatus described in the above-given JP-A publications do not consider discrimination between the foreign particles on the surface of a sample and the foreign particles or defects within the sample before measuring those foreign particles and defects, and its depthwise resolution with which the foreign particles or defects located at a depth within the sample are detected is about the diameter of the radiated light beam or the depth of field (1 µm or above). Therefore, since defects cannot be selectively detected from within a region that is located at a depth of 0.5 µm or less from the silicon surface in which devices such as LSIs are built up, the detrimental defects that causes devices to be defective cannot be selectively detected from the silicon substrate having internal defects, and thus adversely affect the quality control in the process for producing devices such as LSIs.

Accordingly, it is an object of the invention to provide an inspection apparatus for and inspection method of inspecting samples such as substrate materials and capable of discriminating among the foreign particles or. the surface, internal defects in the near-surface region of the substrate and internal defects within a deeper region than the near-surface region, thereby improving the quality control in the device producing process, and also provide a method of production of semiconductor devices using them. It is another object of the invention to provide a standard sample for correcting the detection precision and detection sensitivity in the inspection apparatus and method, and provide a method of producing the same.

In order to achieve the objects of the invention, light is radiated on the surface of a sample, so that the foreign particle on the surface and the defect present within the sample are discriminated from each other by utilizing the difference between the scattered light rays coming back from the sample when the light is radiated on the sample, and that the depth at which the defect is located within the sample is measured with a resolution equivalent to less than the wavelength of the radiated light by utilizing the intensity attenuation of the radiated light within the sample, which attenuation depends on the wavelength of the radiated light (scattered light). Specifically, there is provided an inspection apparatus which includes a light source unit having at least one light source, a first optical system for causing the light emitted from the light source unit to be focused and directed to the surface of the sample, a stage on which the sample is placed, a second optical system for condensing the scattered light from the surface of the sample, means for separating the light condensed by the second optical system into light rays in a plurality of light paths, a plurality of detectors for detecting those light rays, and arithmetic means for computing signal intensity ratios from the light signals which are detected by the detectors. The first and second optical systems are arranged for their axes to respectively make different angles (hereinafter, referred to as incident angles) relative to the normal to the sample surface, and for their axes to make an angle of 50° to 120° relative to each other. In this apparatus, it is desired to provide means for making the sample surface be scanned with light. The scanning means may be any one of a stage moving driver and a light beam deflector.

The foreign particle on the sample surface and the defect within the sample are discriminated from each other by utilizing both the polarized light components which are respectively perpendicular and parallel to an imaginary plane (hereinafter, referred to as observation plane) made by the optical axis (for radiated light) of the first optical system and the optical axis (for detected scattered light) of the second optical system. In this case, the radiated light may be any one of circularly polarized light, non-polarized light and linearly polarized light. The scattered light from the foreign particle on the surface or the defect below the surface is separated into a polarized light component (intensity, Iv) that has an electric vector perpendicular to the observation plane, and a polarized light component (intensity, Ih) that has an electric vector parallel to the observation plane by a polarizing prism that is provided at the back of the second optical system as means for separating light into light components in different light paths. It is possible to provide half mirrors for splitting light into light components in different light paths, and filters between the half mirrors and the detectors so as to select polarized light components. The light intensities of the separated polarized light components for each foreign particle are detected by the detectors, the detected signals of the scattered light components having different polarized directions that are separated 90 degrees from each other are supplied to a computer, where the signal intensity ratios Iv/Ih are calculated. Assuming that a polystyrene-converted particle diameter of the foreign particle on the surface determined from Iv value by Mie scattering theory is smaller than 0.5 µm, for example, it is decided that foreign particle has been detected if the intensity ratio Iv/Ih is larger than 0.3 and it is decided that an internal defect has been detected if the intensity ratio Iv/Ih is less than 0.3. In this case, it is desired to previously compute the scattered angle and intensity ratios Iv/Ih for different polarization directions of the scattered light rays, and discriminate the surface information from the internal information by referring to these values and the data measured by the above method. The irradiation direction may be substantially perpendicular to the sample surface or diagonal to the surface.

The radiated light is the light including a first wavelength that is less attenuated within the sample (, or easy to penetrate the sample) and a second wavelength that is much attenuated within the sample (, or easy to be absorbed by the sample). This radiated light may be generated by adding the light rays from light sources for those wavelengths at a stage before the first optical system or by use of a light source for the first wavelength and means for generating a harmonic of this light ray. The sample surface is scanned by the radiated light preferably in the same way as in the case where the foreign particle on the surface is discriminated from the internal defect. The scattered light coming back from the sample is condensed by the second optical system. The second optical system desirably has an object lens with its chromatic aberration reduced for the two wavelengths of the radiated light. The scattered light condensed by the second optical system is separated into the wavelengths which are detected by the optical detectors. The depth of the internal foreign particle or defect within the sample can be derived from the signal intensity ratio of the two detected wavelengths, by referring to the relation between the depth and signal intensity ratio hat is previously calculated from the attenuation coefficients of the sample to the wavelengths.

The scattered light intensity may be measured by a heterodyne detection method. According to this method, a reference light ray and the scattered light from a defect which are coherent and slightly different in frequency interfere with each other to produce a beat signal of which the amplitude is found for each of the first and second wavelengths, and the scattered light intensity is determined by the square of the amplitude of the beat signal.

The first wavelength λ1 and second wavelength λ2 of the radiated light are selected to meet the following relation. In other words, if the defect measurable region of the sample is assumed to be within depth Z below the surface, and if the depths to which the wavelengths $\lambda 1$, $\lambda 2$ enter into the sample are represented by $\Gamma 1$ and $\Gamma 2$, respectively, then the attenuation of the wavelength $\lambda 1$ of the radiated light at the depth $\Gamma 2$, $\Gamma 1 > \Gamma 2$ can be neglected, and $\Gamma 2 \sim Z$ is satisfied.

Moreover, it is desired to provide a filter at or after the second optical system in order to remove the effect of fluorescence generated when the second wavelength of the radiated light is absorbed by the sample. Also, the first and second wavelengths, when radiated on the sample, may be deviated from each other with respect to time. In this case, the two wavelengths may be alternately and intermittently radiated by use of the first optical system or a chopper provided before it or the two wavelengths may be slightly deviated in the scanning direction so that as shown in FIG. 14, the first-wavelength light is radiated first on a defect and the second-wavelength light radiated second with respect to time as the sample surface is scanned.

When the internal information within the sample is acquired with a resolution higher than the wavelengths of the scattered light and with the near-surface region and the deeper region discriminated from each other, a plurality of light-path splitting means, for instance, may be provided after the second optical system, so that at least one of the first and second wavelengths of the detected light rays is further detected for each polarized light component, whereby the surface information and the internal information can be discriminated at the same time.

The particle size can be determined from the measurements of the external foreign particle on the sample and the internal foreign particle or defect within the sample as follows. The intensity of the scattered light from a defect depends on the shape, complex refractive index (inherent in its material) and size of the defect. Thus, if the foreign particle on the surface and the defect below the surface are assumed to be spheres, and if the foreign particle or defect is made of a certain material so that the complex refractive index can be determined, the diameter of the foreign particle or defect can be estimated from the measured intensity of the scattered light. This method, which is already employed for measuring the dust size by a air-dust monitor or liquid-dust monitor, can also be applied to the measurement of the internal defect. If the silicon substrate for production of LSIs is inspected about the internal defect, the defect size can be calculated from the scattered light intensity provided that the defect is a sphere and made of a material, $SiO_2$. In addition, the particle size may be estimated by use of the complex refractive index of a material other than $SiO_2$ from the beginning, if necessary. If it is assumed that there is a bubble within Si, the refractive index of the scattering body is selected to be 1, and the particle size is determined from that. On the other hand, the size of the foreign particle on the surface can be estimated on a polystyrene conversion basis, or by converting it to the polystyrene equivalent.

Since the inspection apparatus or inspection method utilizes the scattered light from the foreign particle on the surface or the foreign particle or crystal defect within the sample, the standard samples given in the prior art are not suited for this purpose. Even though the particle image transferred to the substrate surface and the polystyrene particle fixed on the silicon surface with siloxane in a sample are compared with the silicon internal defect particle of the same size, their light scattering cross-sections are different since the surroundings of the fine particles have different refractive indexes, and thus the actual signal intensities are different.

Therefore, the standard sample suitable for use in the apparatus for measuring the internal defect is produced by the semiconductor production technology so as to have a structure which has a base material and at least one region in which a plurality of particle-shaped portions with different refractive indexes are formed at a substantially constant depth from the surface. Specifically, a fine pattern of a plurality of particle-shaped portions (different in refractive index from the base material) of the same material as the objects to be detected is formed on the substrate that is made of the same material (base material) as the sample to be observed. In addition, a thin film of the same material as the substrate is formed over the pattern, making the pattern be buried in the interior. The fine pattern thus formed is used for the standard sample of crystal defects. It is desirable to control the thin film depositing condition so that the depth at which the pattern is buried is smaller than the wavelength of the radiated light. The apparatus for measuring crystal defects is corrected for its detection sensitivity and depth resolution by this standard sample, and used for measuring crystal defects. The standard sample may be produced to have a plurality of patterns buried at different depths.

The inspection apparatus and method can also be used in each manufacturing process for semiconductor devices as described below. When the wafers are accepted, inspection is made of whether the surface density of foreign particles on the surface and the concentration of internal defects meet the necessary standard values or not. After the impurity diffusion heat treatment process is finished following the ion implantation, part of a device structure such as the junction in semiconductor devices is formed in a portion of the scribe region on the wafer during a series of processes for semiconductor devices or at the time of having completed the devices. Then, the above measuring apparatus is used to inspect that device structure portion while a crystal defect within a depth of 0.5 $\mu$m from the surface and a foreign particle on the surface are discriminated from each other. At this stage, when it is found from the inspection of defects in the near-surface region that there are defects that are extinguishable by a proper treatment (for example, heat treatment), or there are wafers of which the defect density does not meet the standard value but can be reduced, these wafers are once removed from the production line, heated, and again inspected for those defects. If the defect density meets the range of standard values, the corresponding wafer can be fed back to the line as a non-defect product.

The function of the inspection apparatus and method of the invention will be described on the basis of the knowledge about optics. The scattering of radiated light from the surface of the sample or the interior of the sample has been referred to "Principle of Optics" written by M. Born, E. Wolf (published by the Tokai University in 1975).

The inspection apparatus of the invention has the feature that, as described later in detail for each function, defect measurement is made while the foreign particles on the sample surface are discriminated from the foreign particles or crystal defects within the sample by utilizing the difference between the scattered light rays from those particle and defects, or by the side scattered light from the former and the backward scattered light from the latter. Therefore, it is important to set an angle (detection angle) at which the optical axis of the first optical system for causing light to be directed to the sample intersects with that of the second optical system for condensing the light from the sample on the sample surface. In other words, when the detection angle is too small, the foreign particle on the surface is also measured as the backward scattered light, thus making it impossible to discriminate the external foreign particle from the internal defect. In addition, when the optical systems are arranged for their optical axes to be symmetrical to the normal to the sample surface, the radiated light is reflected from the sample surface to increase the background signal which has adverse effect on the measurement. In order to solve these problems, according to the invention, the first and second optical systems are arranged to meet the condition that the angles of the optical axes of the optical systems to the sample surface are different from each other (, or both the optical axes are not symmetrical to the normal to the sample surface), and that the difference between the incidence angles of the optical axes to the surface (, or detection angle) is between 50° to 120°.

The apparatus according to the invention has the function for discriminating the foreign particle on the surface from the internal defect. This function will be described with reference to FIGS. 1 and 2. In FIGS. 1 and 2, like elements corresponding to those of the embodiment 1 shown in FIG. 15, which will be described later, are identified by the same reference numerals. FIG. 1 shows the situation in which detection is made of the scattered light from a foreign particle 4 on the surface of a sample 14, and FIG. 2 shows the situation in which detection is made of the scattered light from a defect 21 within the sample 14. Here, the sample is a silicon wafer, and a light ray 2 emitted from a light source 1 is circularly polarized laser light. As shown in the two figures, the same irradiating (first) and detecting (second) optical systems 3, 5 can be used, and the angle of the scattered light in the case where the foreign particle on the surface is detected is different from that in the case where the internal defect is detected. In other words, the detection angle of the scattered light from the internal defect is shifted, by an angle that it is refracted at the interface between the air and the silicon, toward the backward scattered angle region. If the angular range for the external foreign particle is represented by (θ1s~θ2s), and the angular range for the internal defect by (θ1i~θ2i), then the relation between θ1s and θ1i and the relation between θ2s and θ2i are expressed by the following equation (1) by Snell law (n is the refractive index of the silicon wafer, and x is 1 or 2).

$$\theta xi = 180° - \arcsin[\sin(180° - \theta xs)/n] \quad (1)$$

If the measurement is made by the first and second optical systems 3, 5 that are arranged so that the detection angle θd is 75° as shown in FIG. 1, the scattered center angle θc of the scattered light from the foreign particle 4 on the surface is 105°, thus it can be said that the side scattered light is detected. As illustrated in FIG. 2, when the optical systems are arranged in the same way as in FIG. 1, the scattered angle of the scattered light from the defect within the silicon wafer is 164.5 degrees since the refractive index n of silicon and that n of the air are 3.56 (to the wavelength, 1064 nm) and 1.0, respectively, thus it can be said that the backward scattered light is detected. Therefore, the information about the surface of the sample and the information about the interior of the sample can be extracted as side scattered light and backward scattered light by selecting such a proper detection angle, and the two kinds of information can be discriminated by utilizing the difference between the polarization degrees of light due to the scattered angles. According to Rayleigh scattering theory which describes the scattering phenomenon of light from a much less particle than its wavelength, it is known that when non-polarized light is radiated on a fine particle, the side scattered light is polarized in the direction perpendicular to the observation plane, and the backward scattered light is non-polarized.

Thus, on the basis of the knowledge of Rayleigh scattering theory, the ratio P=Iv/Ih (P value) was computed with the diameter and refractive index of the fine particle being changed under the condition that the radiated light wavelength: 1.064 μm, the aperture number of detecting lens (N.A. value): 0.1, the side scattered center angle θc: 105° and the backward scattered center angle θc: 164.5°. The results are shown in terms of contour lines in FIGS. 3 and 4. Here, it should be noted that in FIG. 3 for the detection condition to the foreign particle on the surface, P>0.3 when the particle size is 0.5 μm or below and that in FIG. 4 for the detection condition to the internal defect, P is about 1 almost independently of the particle size and refractive index (in this range of computation the minimum value is 1.01, and the maximum value is 1.57). FIG. 5 shows the scattered-angle dependency of the relative differential scattering cross-section when the defect size is much smaller than the wavelength of the radiated light. The solid line indicates the differential scattering cross-section to the scattered light of which the electric vector has a polarized component perpendicular to the observation plane, and the broken line indicates the differential scattering cross-section to the scattered light of which the electric vector has a polarized component parallel to the observation plane. From FIG. 5, it will be understood that when we directs our attention to the difference between the scattered-angle dependency of the differential cross-section cross-sectional area to the intensity Iv of the scattered light of which the electric vector has a polarized component perpendicular to the observation plane and that to the intensity Ih of the scattered light of which the electric vector has a polarized component parallel to the observation plane, the side scatted light from a foreign particle on the surface of the sample can be discriminated from the backward scattered light from the internal defect by the intensity ratio Iv/Ih. If this differential scattered cross-section area is integrated with respect to the scattered solid angle with the normal to the sample surface as its center, the computed scattered cross-section is found to be proportional to the scattered light intensity. FIG. 6 shows the scattered-angle dependency of the differential scattering cross-section when the foreign particle on the surface is as large as about a half of the wavelength of the scattered light (the wavelength of the scattered light: 1.064 μm, and the foreign particle on the surface: a polystyrene particle (refractive index, 1.59) of 0.5-μm diameter). The solid line and broken line respectively indicate the same as in FIG. 5. Thus, it has been theoretically proved that even though the foreign particle on the surface is a polystyrene particle of less than 0.5-μm diameter, the foreign particle on the sample surface and the internal defect within the sample can be discriminated by the ratio Iv/Ih.

On the other hand, when the scattered light from the internal defect 21 exits from the silicon substrate into the air, its component perpendicular to the observation plane is chiefly reflected below from the interface as shown in FIG. 7, so that the intensity of the scattered light is reduced to about 20%. FIG. 8 shows the relation between the reflection factor of each polarized component of the scattered light to the interface and the incident angle θ of the scattered light that comes from the defect and reflected from the interface within the silicon. From FIG. 8, it will be understood that since the reflection factor of the polarized component perpendicular to the observation plane is about 80% when the incident angle is 15.5 degrees (that is, the angle of this component exiting from the surface is 75 degrees, and the scattered angle is 164.5 degrees), the intensity of the exiting and detected light is reduced to about 20%. In addition, since the reflection factor of the polarized component parallel to the observation plane is substantially 0%, the scattered light from the defect arrives at the detector with no attenuation. Therefore, the measured intensity ratio P of the polarized components of the scattered light from the defect that is present within the substrate is about 20% of the P value determined from FIGS. 4 to 6, or 0.2<P<0.3. Thus, if the diameter of the detected particles is limited to 0.5 μm or below, the P value smaller than 0.3, or P<0.3 indicates the internal defect, and the P value larger than 0.3, or P>0.3 indicates the external foreign particle on the surface. Since this P value actually depends upon the inherent factors of the apparatus, it should be corrected according to the design of the apparatus.

As is clear from the above description, it is important to determine the arrangement of the first and second optical systems on the basis of the scattered-angle dependency of Iv and Ih shown in FIGS. 5 and 6 and the incidence-angle dependency of Iv and Ih, shown in FIG. 8, of the scattered light that propagates in the sample and incident to the surface. While FIGS. 5 and 6 show the conditions by which the foreign particle on the sample surface and the internal defect can be discriminated, with the scattered angle θc changed as a parameter, the important thing is that when the inspection apparatus is actually constructed, the first and second optical systems are arranged to meet the detection angle θd (defined as θd=180°−θc) associated with the illustrated region of θc. It is also important to consider the conditions of the internal reflection of the scattered light from the interior of the sample relative to the detection angle, or the incidence angle dependency of Iv and Ih shown in FIG. 8. From these conditions, it will be found that the first and second optical systems are required to be arranged for the detection angle θd made by their optical axes to be at least within the range from 50° to 120°. In this connection, the optimum region of the detection angle is present between about 70° and 100° depending upon the construction of the apparatus.

While light is radiated from the optical system along substantially the normal to the sample surface as described above, the external foreign particle and internal defect can be substantially similarly discriminated even by oblique irradiation of light from the optical system to the sample surface. For reference, the optical system for the diagonal irradiation will be described with reference to FIGS. 9 and 10. In FIGS. 9 and 10, the sample 14 is a silicon substrate and the radiated light 2 is circularly polarized laser light, as is similar to those shown in FIGS. 1 and 2. As illustrated in FIGS. 9 and 10, the detection solid angle of the scattered light from the foreign particle 4 on the sample surface is different from that of the scattered light from the defect 21 within the sample. Here, if the scattered angle θ is defined with respect to the direction of travel of the radiated light, the scattered light to be detected from the foreign particle on the crystal surface is reflected sideways in the direction of slightly less than about 90 degrees as shown in FIG. 9, and the scattered light to be detected from the defect within the crystal is reflected backward in the direction of about 180 degrees as shown in FIG. 10. Thus, if the light intensity Iv of the scattered polarized component having an electric vector perpendicular to the observation plane is compared with the light intensity Ih of the scattered polarized component having an electric vector parallel to the observation plane by referring to FIG. 5, it will be found that Ih<Iv for the scattered light from the foreign particle on the crystal surface and that Ih is substantially equal to Iv for the scattered light from the defect within the crystal. In addition, when light of 1.064-μm wavelength is radiated on the silicon crystal (refractive index, 3.56) at an incident angle of 75 degrees, about 77% of the polarized component having an electric vector perpendicular to the observation plane is reflected therefrom, whereas only 0.2% of the polarized component parallel to the observation plane is reflected therefrom. Thus, by considering this fact, the condition of Ih>Iv is satisfied for the scattered light from the defect within the crystal. When the circularly polarized light of 1.064-μm wavelength is radiated on the silicon crystal (refractive index, 3.56) at an incident angle of 75 degrees, and when the scattered light in the direction of the normal to the crystal surface is condensed by a lens of aperture number, 0.4 in the optical systems shown in FIGS. 9 and 10, the detectors can detect the scattered light reflected from the foreign particle on the crystal surface over the angular range from about 81° (θ1) to about 129° (θ2), and the scattered light reflected from the defect within the crystal over the angular range from about 158° (θ1') to about 171° (θ2'). While the detection angle in this example was set at 75°, the same scattered angle deviations occur even for the other samples having different detection angles and reflection factors. Therefore, the foreign particle on the surface and the internal defect can be discriminated by setting the detection angle as in the optical systems shown in FIGS. 1 and 2 in view of the difference of the scattered angle dependency between Iv and Ih shown in FIGS. 5 and 6 and the difference of the internal reflection to the crystal interface between Iv and Ih as shown in FIG. 8.

While the radiated light is circularly polarized laser light in the above description, it has polarized light components perpendicular and parallel to the observation plane, and it may be other than the circularly polarized light if the intensity ratio between the polarized light components is known. If the measured Ih and Iv are corrected using the intensity ratio, the conditions can be analyzed in the same way as when the circularly polarized light is radiated.

Moreover, even when the foreign particle on the surface of a amorphous silicon film for use in liquid crystal displays and the defect below the surface are measured and discriminated, the discrimination method according to the invention can be applied as well as for the crystal silicon, since the refractive index is as large as 3.59 (to the wavelength, 1064 nm).

Description will be made of the principle of measuring with a resolution of less than the wavelength the depth at which a defect is located near to the sample surface within the sample by the inspection apparatus and method of the invention with reference to FIGS. 11, 12 and 13. The depth Γ to which the incident light enters into the surface of the sample to be attenuated to 1/e of the amplitude at the surface is given by $$\Gamma = \lambda/2\pi k \qquad (2)$$

where λ is the wavelength to which the refractive index of the material of the sample is n, and k is the attenuation rate. Therefore, the light incident to the substance at an incidence angle θ from the air side is attenuated by $\exp((-2Z/\Gamma)\cos(\arcsin(\sin\theta/n)))$ at depth Z from the surface as compared with the intensity at the surface. Thus, such a case will be considered that radiated light is incident to the sample surface at an incident angle θ from the air side, scattered by the defect within the sample toward the sample surface, and detected at a solid angle above the surface, if the integrated scattering cross-section of the defect relative to the solid angle for the detection is represented by σ, and the intensity of the incident light by I, the intensity S of the scattered light from he defect located at the depth Z from the material surface can be expressed by the following equation.

$$S = I\sigma \exp[-(2Z/\Gamma)(1+1/\{\cos(\arcsin(\sin\theta/n))\})] \quad (3)$$

If, now, the refractive indexes of the sample to the wavelengths λ1, λ2 are represented by n1, n2, the penetration depths by Γ1, Γ2, the incident light intensities by I1, I2, the intensities of the scattered light measured by S1, S2, and the integrated scattering cross-section by σ1, σ2, the following equations can be satisfied.

$$S1 = I1\sigma1 \exp[-(2Z/\Gamma1)(1+1/\{\cos(\arcsin\theta/n1))\})] \quad (4)$$

$$S2 = I2\sigma2 \exp[-(2Z/\Gamma2)(1+1/\{\cos(\arcsin(\sin\theta/n2))\})] \quad (5)$$

Thus, the depth Z of the defect is given by the following equation.

$$Z = C1 \, \ln[C2(S1/S2)(\sigma2/\sigma1)] \quad (6)$$

where C1 and C2 are formed of apparatus constants and optical constants of the sample, and defined by the following equations.

$$C1 = 1/[(2/\Gamma2)(1+1/\{\cos(\arcsin(\sin\theta/n2))\})] - (2/\Gamma1)(1+1/\{\cos(\arcsin(\sin\theta/n1))\})] \quad (7)$$

$$C2 = I2/I1 \quad (8)$$

In order to find the depth of the defect in this invention, it is necessary to first determine the size of the defect. If light of wavelength λ1 capable of penetrating the sample, or light of wavelength λ1 having an unlimited value of Γ1 is used in Equation (4), the incident light intensity I1 and scattered light intensity S1 are not decreased within the crystal, and thus the integrated scattering cross-section σ1 relative to a certain detection solid angle can be expressed by $$\sigma1 = S1/I1 \quad (9)$$

In this case, if Γ1 is infinity, C1 can be approximated as $$C1 = 1/[2/\Gamma2)(1+1/\{\cos(\arcsin(\sin\theta/n2))\})] \quad (10)$$

While light of wavelength Λ1 is assumed to be capable of penetrating the crystal in this case, it may be assumed that Γ1>Γ2 and that the light of wavelength λ1 is almost not attenuated at depth Γ2, in order that Equations (9) and (10) can be satisfied within the measurement range. For example, the depths Γ1, Γ2 to which light of different wavelengths enter into the crystal may be ten times or above different from each other. If the integrated scattering cross-section σ1 is known, the particle size can be estimated by deciding the refractive index of the defect and by Mie scattering theory. In this invention, the refractive index of $SiO_2$ particle is assumed to be 1.45 as described above. If the particle size is known, it is possible to find the integrated scattering cross-section σ2 for a detection solid angle to light of wavelength λ2 to be absorbed by the sample, and hence the ratio σ1/σ2 of the integrated scattering cross-sections can be determined. By substituting this into Equation (6), it is possible to obtain the depth Z. FIG. 21 shows the above actual flow of data analyzation. In this figure, the direct detection mode corresponds to the above analysis, the first penetrating wavelength is 1064 nm, and the second absorbed wavelength is 532 nm. The precision of measurement on the depth will be described in accordance with the procedure for the analysis. FIG. 11 is a graph showing the relation between the attenuation of the radiated light of each wavelength and the depth from the surface of silicon, measured by use of refractive index n of silicon=4.15 to wavelength 532 nm, attenuation rate k=0.044, refractive index n of silicon=3.56 to wavelength 1064 nm, and attenuation rate k=0.0022. Also, the measurements to light of wavelength 488 nm are shown in this figure. The refractive index n of silicon to this wavelength is 4.367, and attenuation rate k of the light is 0.079.

FIG. 12 is a graph showing the ratio S2/S1 of the intensity S2 of light of wavelength 532 nm to the intensity S1 of light of wavelength 1064 nm which are determined from FIG. 11. Here, the ratio on the surface is 1. Also, the ratio S3/S1 of the intensity of light of wavelength 488 nm to the intensity S1 of light of wavelength 1064 nm is shown in this figure.

FIG. 13 is a graph showing examples of signal waveforms of the scattered light intensities obtained by irradiating laser light beams of wavelengths 1064 nm and 532 nm on the silicon while scanning the same positions. Thus, the ratio S2/S1 is determined, and the depth can be found from the ratio S2/S1 by use of the relation shown in FIG. 12.

Here, we shall consider the effect of the change of the absorption coefficient due to the impurity diffusion in silicon on the inspection method according to the invention. When the amount of doping a silicon substrate is in the order of $10^{15}$ per $cm^3$, the change of the absorption coefficient due to the doping can be neglected. However, in the device forming region, the amount of doping sometimes exceeds $10^{20}$ per $cm^3$. After the measurement by ellipsometer, the attenuation rate of the wavelength 633 nm in this region was found to be increased to 0.055 (as compared with 0.022 without doping). However, since the diffusion layer in the device forming region is about 0.1 μm thick, the absorption rate in the 0.1-μm thick region of attenuation rate 0.055 is about 10%, and thus the effect on the inspection method of this invention is negligibly small. Therefore, the inspection method of the invention can also be applied to the device forming region.

The amorphous silicon has refractive index n=4.4 (to wavelength 532 nm), 3.59 (to wavelength 1064 nm), attenuation factor k=0.85 (to wavelength 532 nm), 0.048 (to wavelength 1064 nm). Accordingly, the depth to which light enters into the amorphous is 3.5 μm (wavelength 1064 nm), and 0.1 μm (wavelength 532 nm). Since the amorphous silicon layer of the thin film transistor for use in liquid crystal displays is less than 0.3 μm thick, the attenuation of light of wavelength 1064 nm within this thickness can be neglected. Thus, the particle diameter can be determined by the intensity of the scattered light of wavelength 1064 nm as well as in the crystal silicon, and also the depth can be estimated by the intensity ratio between the scattered light rays of wavelength 1064 nm and a wavelength to be absorbed, for example, 532 nm and by use of Equation (6) as described above.

Since the backward scattered light from a foreign particle or defect within the sample is measured in the method of measuring the depth of a foreign particle or defect near the surface of the sample with a resolution of less than the wavelength, it is necessary to meet the condition under which the backward scattered light can be discriminated from the scattered light from the foreign particle on the surface of the sample. Therefore, it is important that when the inspection apparatus is actually constructed, the first and second optical systems are arranged for their optical axes to meet the detection angle θd relative to the region of θc shown in FIGS. 5 and 6. Specifically, the angle between the two optical systems is required to be set at least between 50° and 120° (the optimum region for the detection angle is between about 70° and 100°) as well as when the surface information and internal information of the sample are discriminated as described above.

The size of the foreign particle or defect can be calculated from the measurements of the foreign particle on the surface of the sample and the foreign particle or defect within the sample, the intensity of the scattered light from the fine particle, the shape, material (refractive index and absorption factor) and size of the particle on the basis of Mie scattering theory (Ann. Phys., vol. 25 (1908), pp. 377 to 445). Thus, in order to precisely determine the size, it is necessary to acquire information of the shape and material of the defect. However, it is difficult to optically measure the shape and material of the foreign particle or defect of submicron meter size on the surface of or within the sample to be inspected. Also, it is not practical to previously measure the shape and material by another means since the number of defects to be measured is large. Thus, in this invention, the size of the foreign particle on the surface is estimated on a polystyrene particle conversion basis, as is similar to the case where it is determined by the conventional surface defect measuring apparatus. Moreover, when the sample to be measured is a silicon wafer, the size should be computed from the scattered light intensity after it is assumed that the internal defect is spherical and that the material is $SiO_2$. The most of the silicon crystal substrates used for the production of LSIs are produced by crystal pulling method called CZ method. Since this crystal contains supersaturated oxygen, $SiO_2$ particles are educed as internal defects within the substrate by various kinds of heat treatment when LSIs are produced. In addition, it is known that most of the $SiO_2$ particles have a diameter of 0.2 $\mu$m or below which is much less than the wavelength, 1.064 $\mu$m of the radiated light in this invention. In that case, the scattered light intensity depends on the volume and refractive index of the fine particles, but does not depend on the shape. Therefore, the refractive index is assumed to be a certain value (,or the material of which the particle is made is fixed), the volume of the sphere is determined so that equal scattered light intensity can be obtained, and thus the radius or diameter (particle size) of the sphere can be found. The volume may be estimated, If necessary. This is the reason why the defects are assumed to be $SiO_2$ as the material and to be spherical as the shape in this invention. By this quantification, it is possible that the actual size can be estimated by use of the refractive index and absorption coefficient when the material is found by any method in advance or after the fact. Also, it is effective to determine the size by use of a refractive index other than $SiO_2$ from the start, if necessary.

The standard sample used in the inspection apparatus and method according to the invention has a fine pattern corresponding to defects, and a substrate and thin film in the neighborhood of the pattern, which are the same material as the samples to be measured and formed in the region near the surface. Therefore, if the size of the fine pattern of the standard sample is equal to that of fine defects, the scattered light intensity is the same. Moreover, the fine defects can be formed for their size and buried depth to be quite uniform and well controlled by the highly developed semiconductor production technology.

BEST MODE FOR CARRYING OUT THE INVENTION

Embodiments of the invention will be described detail.

Embodiment 1

Figure 15:
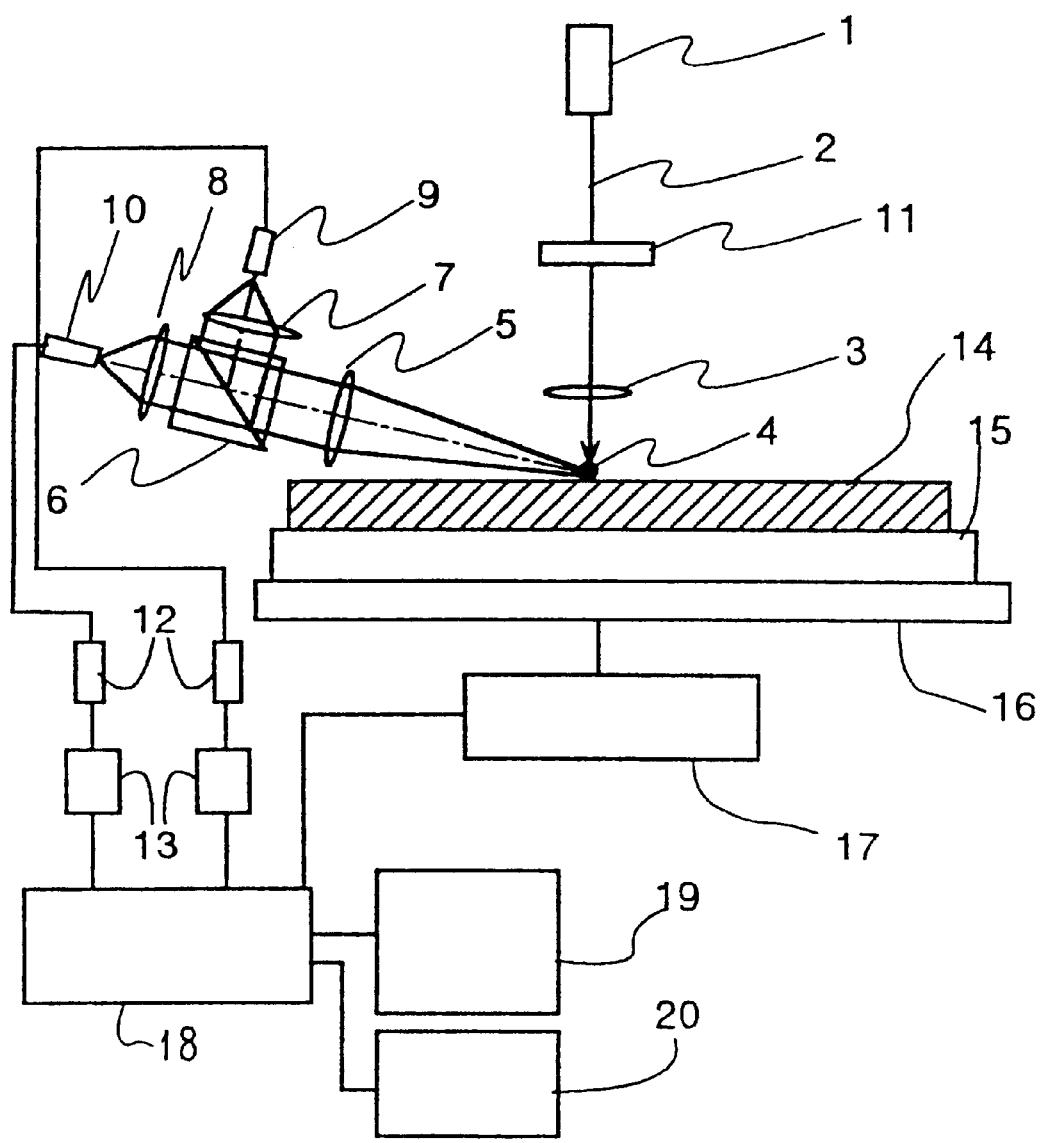
FIG. 15 is a schematic diagram of the construction of the embodiment 1 of the invention.

Description will be made of the construction of an apparatus to be used for the measurement of foreign particles and defects of a silicon wafer with reference to FIG. 15. A linearly polarized laser light beam 2 of a wavelength, 1.064 μm emitted from a YAG laser light source 1 is circularly polarized by a ¼ wavelength plate 11, condensed by a lens 3, and vertically radiated to a silicon wafer 14 as a solid sample being measured. The scattered light from a foreign particle 4 on the silicon surface or a defect (not shown) within the wafer is collected by a lens 5 that is located at an angle of 75 degrees to the irradiation direction, separated into polarized components by a polarization prism 6, and detected. The polarized components in this case include an intensity (Iv) of the component having an electric vector perpendicular to the observation surface and an intensity (Ih) of the component having an electric vector parallel thereto. The separated polarized components are condensed by lenses 7 and 8, and detected by optical detectors 9 and 10, respectively. The detected signals are amplified by amplifiers 12, digitized by A/D converters 13, and supplied to a computer 18. The above measurement is made while the sample is being scanned. This scanning is made by fixing the wafer to a scanning stage 16 through a wafer fastener 15 and moving the scanning stage in the horizontal direction. The wafer fastener has the function to correct the warp of the wafer by a vacuum chuck (not shown). The portion which is made in contact with the wafer is made of high-purity quartz in order to prevent the wafer from being contaminated. The scanning stage is controlled through a driver 17 by the computer 18. The amount of scanning movement is fed to the computer together with the two different signals Iv and Ih. The computer calculates the polystyrene-converted particle diameter by Mie scattering theory from the signal Iv for each detected particle. When the calculated particle diameter is 0.5 μm or below, P=Iv/Ih is computed. If P>0.3, the detected defect is decided to be a foreign particle on the surface. If P<0.3, it is decided to be an internal defect. Here, the $SiO_2$-converted particle diameter is determined for the particle decided as the internal defect. Thus, three kinds of data are displayed on a monitor 19, and printed out by a printer 20. In other words, they are the distribution of foreign particles on the surface, and the distribution of the polystyrene-converted particle diameters; the internal defect distribution, and the distribution of the $SiO_2$-converted particle diameters; and the distribution of particles that cannot be decided if they are foreign particles on the surface or internal defects of 0.5 μm or above in the polystyrene-converted particle diameter, and the distribution of the polystyrene-converted particle diameters. Of course, only part of these information may be acquired or displayed, if necessary.

While in this embodiment P=0.3 is used for the reference to the decision of whether the defect is the foreign particle on the surface or the internal defect, the ratio P is dependent upon the specification of the apparatus used, and thus this value should be corrected on an experimental basis. As an example of this experiment, a standard sample with a polystyrene particle of 0.2 μm in diameter attached on the sample surface is used, and the Iv/Ih ratio is computed from the detected signals and utilized as the decision reference.

Figure 1:
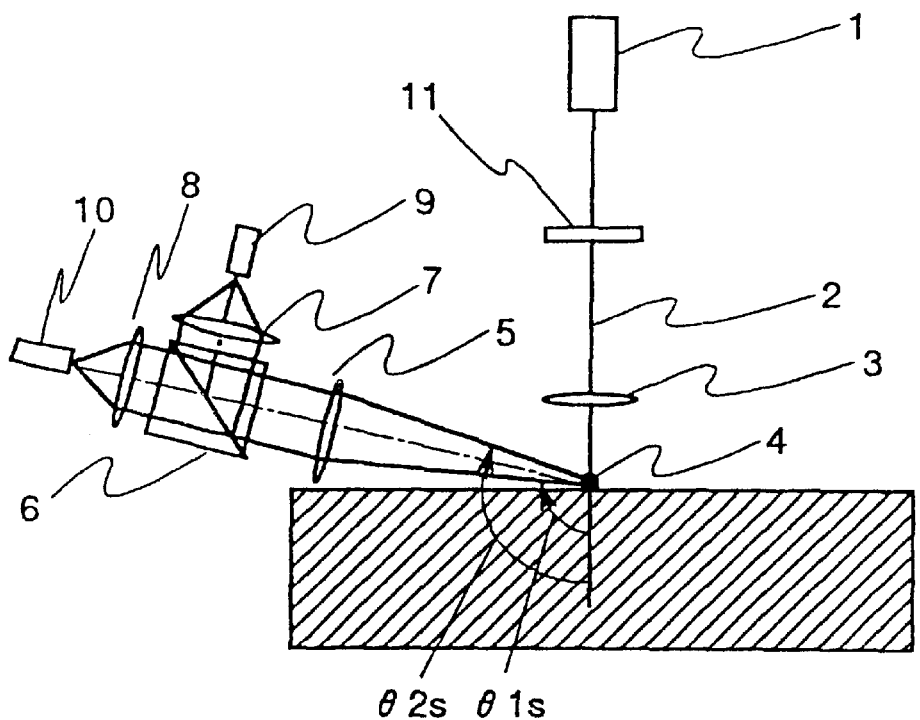
FIG. 1 is a diagram to which reference is made in explaining the detection of scattered light from foreign particles on the surface of a sample, according to the present invention.
Figure 2:
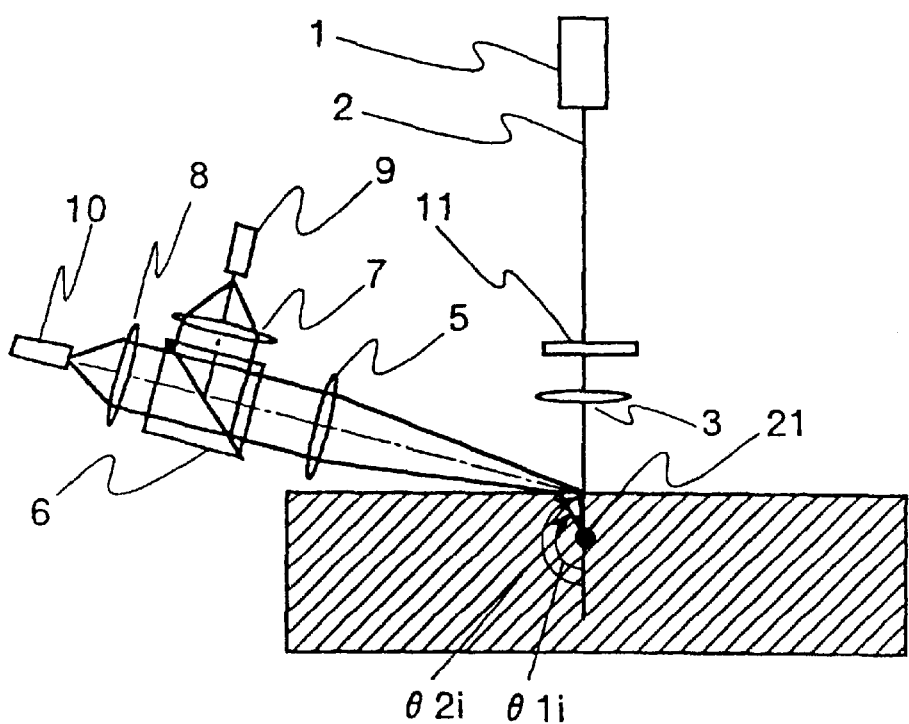
FIG. 2 is a diagram to which reference is made in explaining the detection of scattered light from a defect within the sample, according to the present invention.
Figure 3:
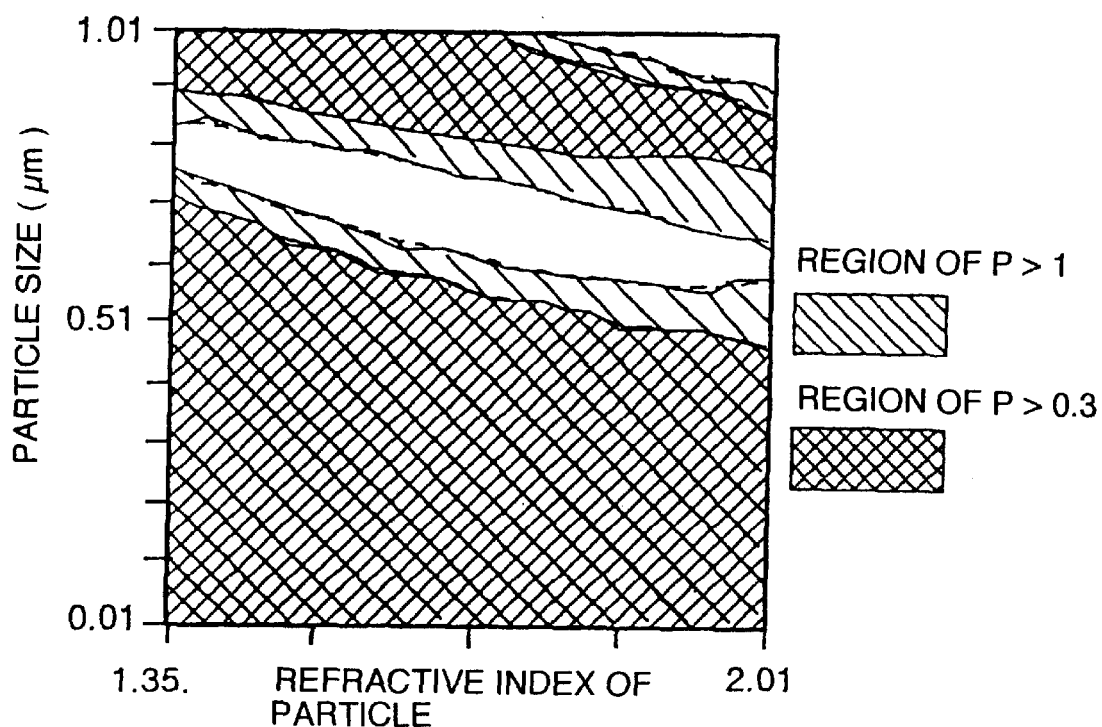
FIG. 3 is a graph showing the dependency of P value in the side scattering by particles on the diameter and refractive index of particles.
Figure 4:
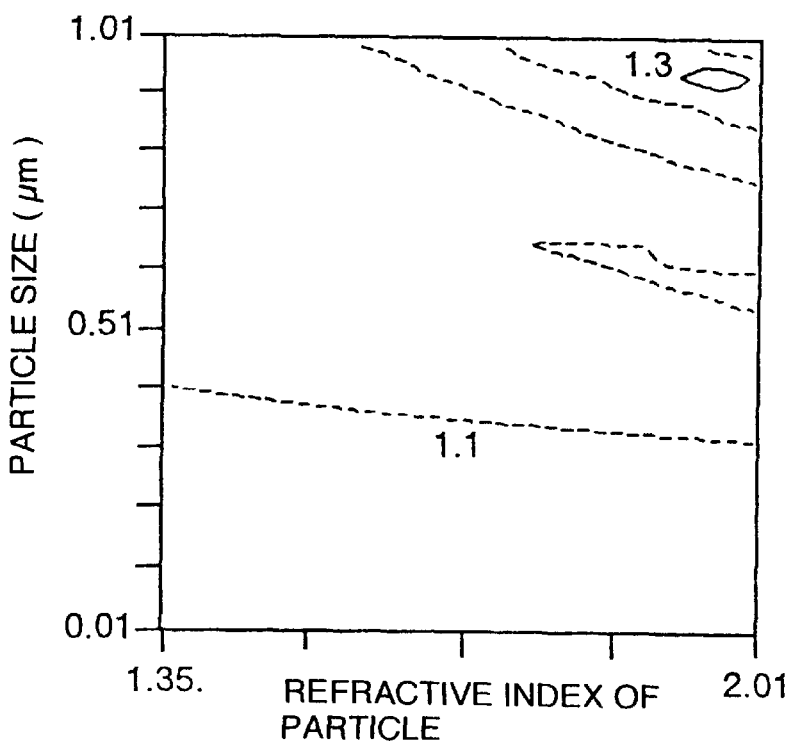
FIG. 4 is a graph showing the dependency of P value in the backward scattering by particles on the diameter and refractive index of particles.
Figure 5:
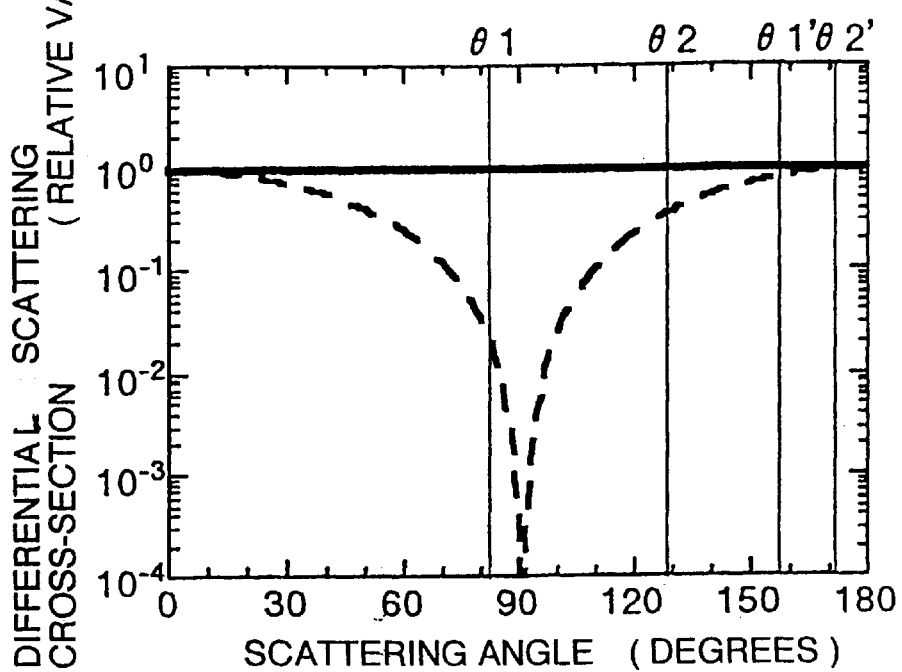
FIG. 5 is a graph showing a scattering angle dependency of the differential scattering cross-section when the scattering body is much smaller than the wavelength of the radiated light.
Figure 6:
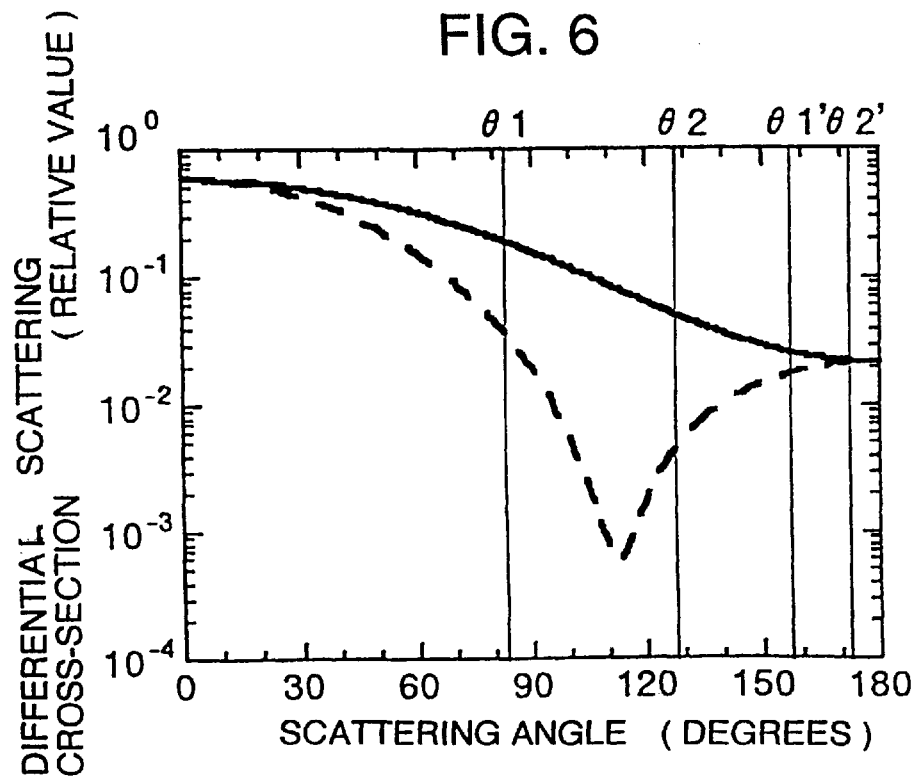
FIG. 6 is a graph showing a scattering angle dependency of the differential scattering cross-section area when the wavelength of the radiated light is 1.064 $\mu$m, and the scattering body is a 0.5-$\mu$m diameter polystyrene particle.
Figure 7:
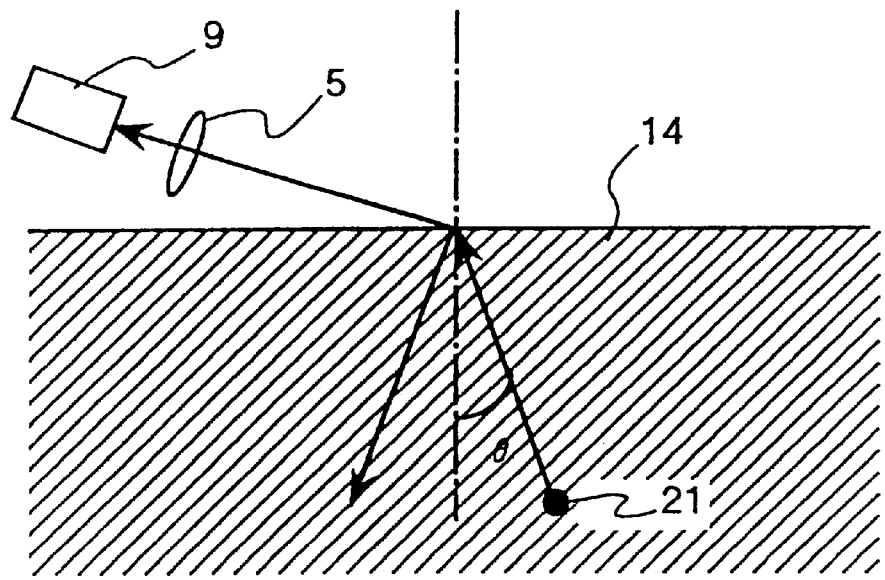
FIG. 7 is a diagram to which reference is made in explaining the reflection of scattered light within the sample.
Figure 8:
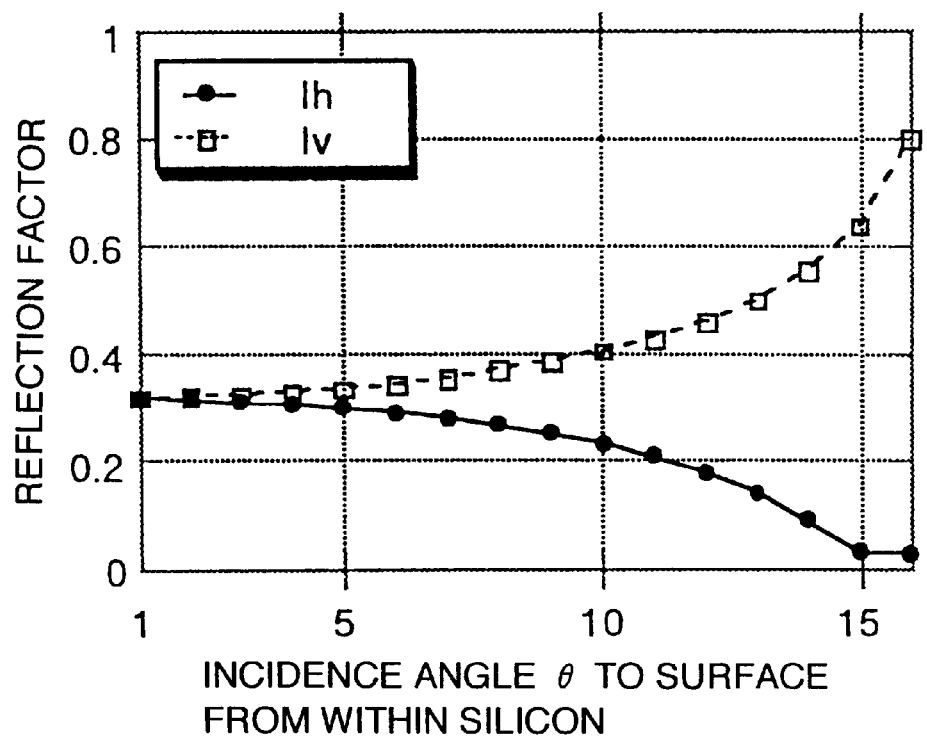
FIG. 8 is a graph showing an incidence angle dependency of the internal reflection factor of the scattered light from the defect within the silicon material.
Figure 9:
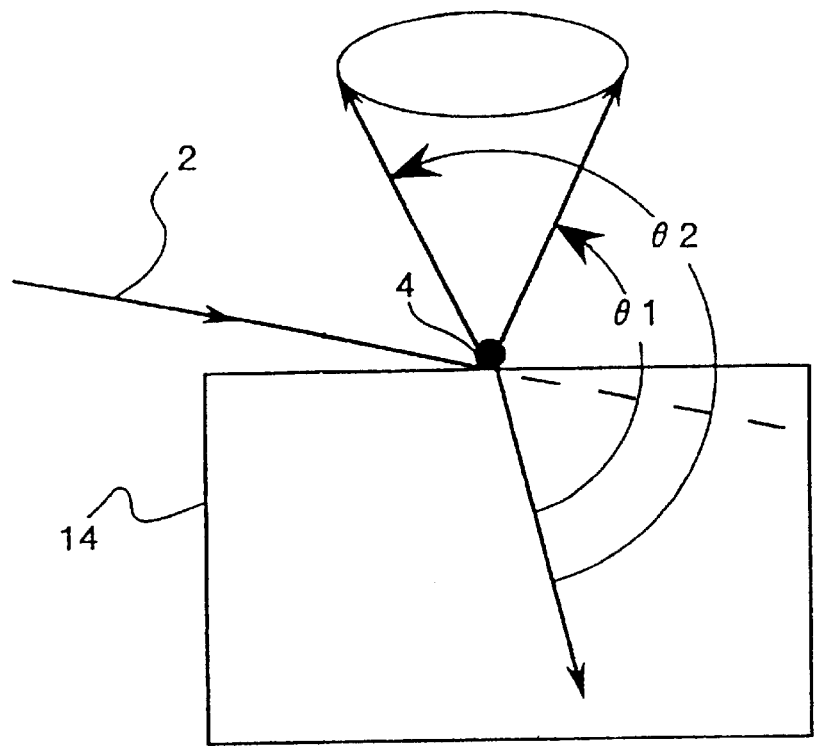
FIG. 9 is a diagram showing the detected solid angle of the scattered light from a foreign particle on the surface of the sample when light is slantly radiated to the sample.
Figure 10:
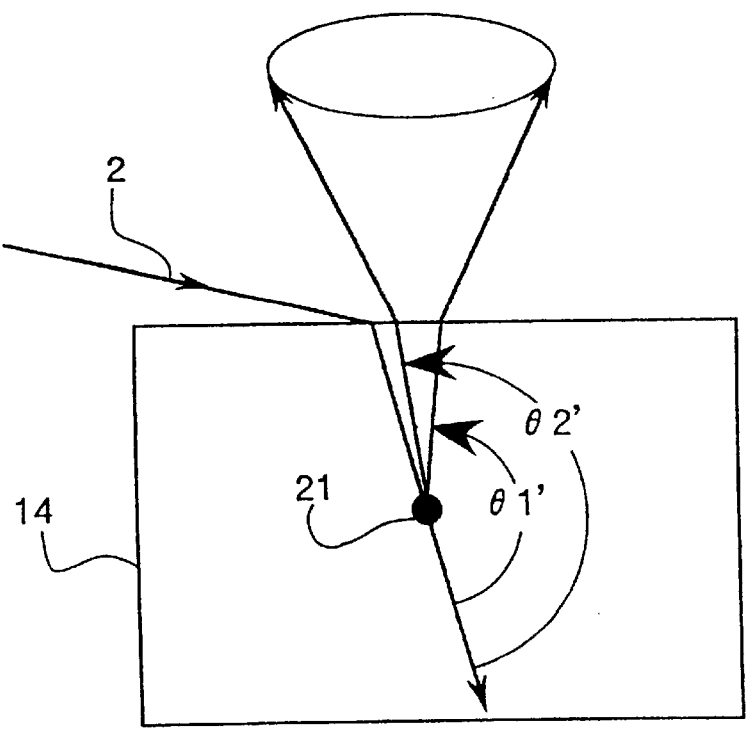
FIG. 10 is a diagram showing the detected solid angle of the scattered light from the defect within the sample when light is slantly radiated to the sample.
Figure 11:
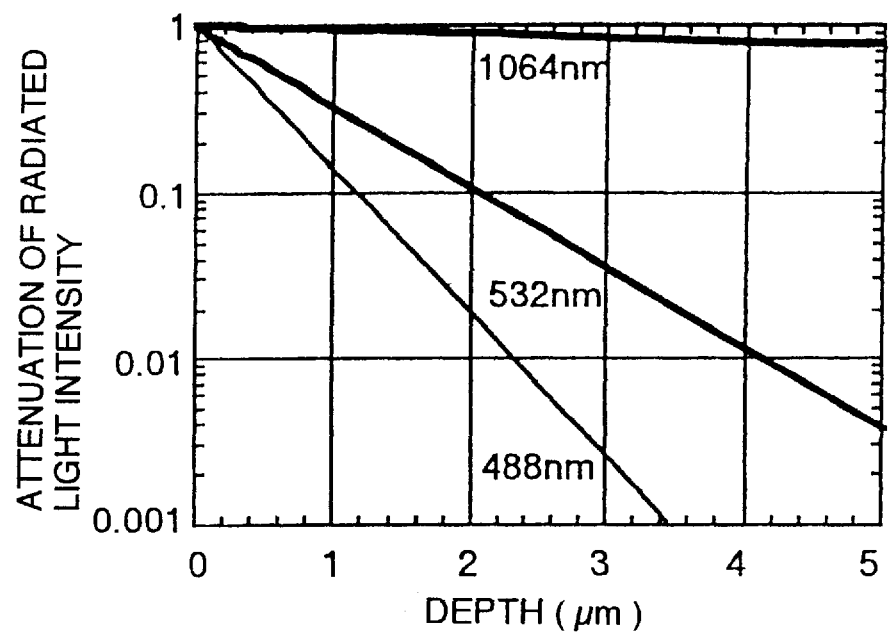
FIG. 11 is a graph showing a depth dependency or the attenuation factor of the radiated light with its wavelength changed.
Figure 12:
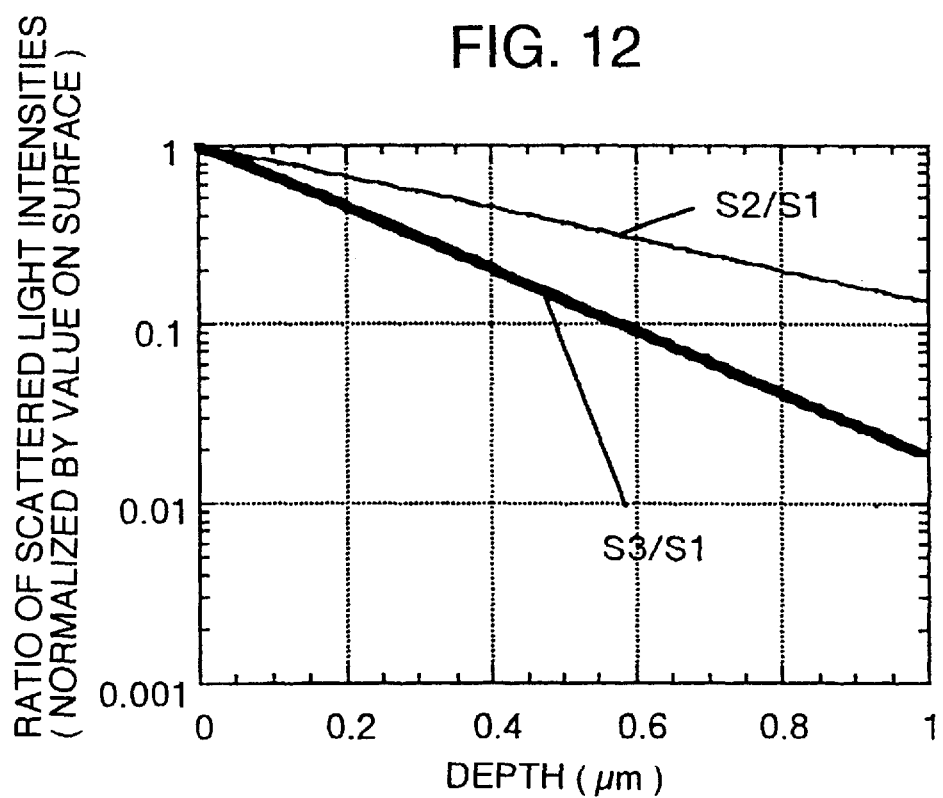
FIG. 12 is a graph showing a depth dependency of the intensity ratio of different-wavelength scattered light rays in silicon.
Figure 13:
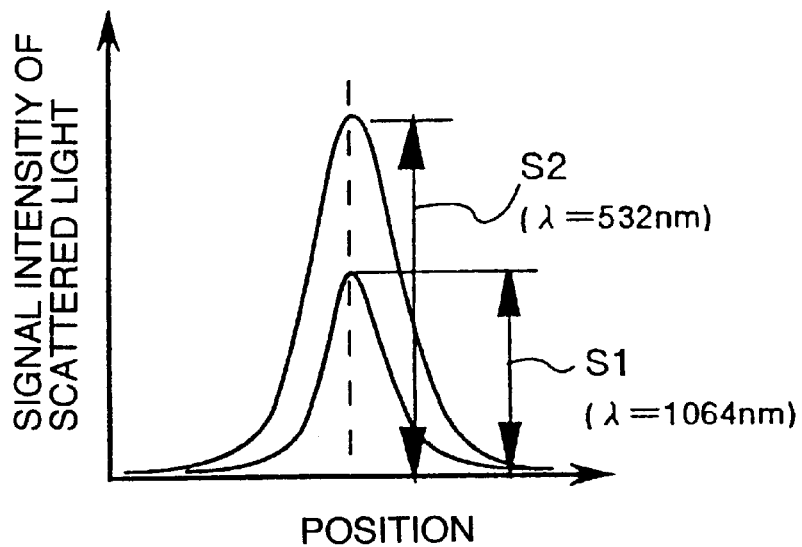
FIG. 13 is a graph showing examples of measurement for the defect within the sample by use of different-wavelength scattered light.

When the sample to be measured and the wavelength of the radiated light are changed in the above embodiment, the same computation as in FIGS. 3 and 4 are performed, determining the range of particle diameters over which the foreign particle on the surface and the internal defect can be discriminated. Thus, they can be discriminated in accordance with the P value within the range of particle diameters as well as in this embodiment. According to our experimental results, when the wavelength of the radiated light was 532 nm, the Iv/Ih ratio was 3.1 for the 0.2-μm polystyrene particle on the silicon wafer surface, and 0.1 to 1.0 for the internal defect. Therefore, the decision reference value Iv/Ih is selected to be 2.0 to 3.0. While the radiated light used in this embodiment is circularly polarized, it may be non-polarized. In addition, the irradiation direction is substantially perpendicular to the sample surface as shown in FIG. 15, the light may be radiated obliquely to the sample surface. In this case, it is important to note that the angle between the irradiation direction and the detection direction is set as near to 90 degrees as possible.

This embodiment has the effect to be able to discriminate between the foreign particle on the sample surface and the internal defect within the sample to an extent of the range within a certain particle diameter and derive an appropriate size distribution of each of the external particle and the internal defect. Therefore, the depth of a defect located within the interior of a crystal material such as a silicon wafer can be precisely measured with a higher resolution than the radiated light wavelength. This embodiment can be applied to the amorphous silicon thin film formed on the transparent substrate that is used for a liquid crystal display.

Embodiment 2

Figure 16:
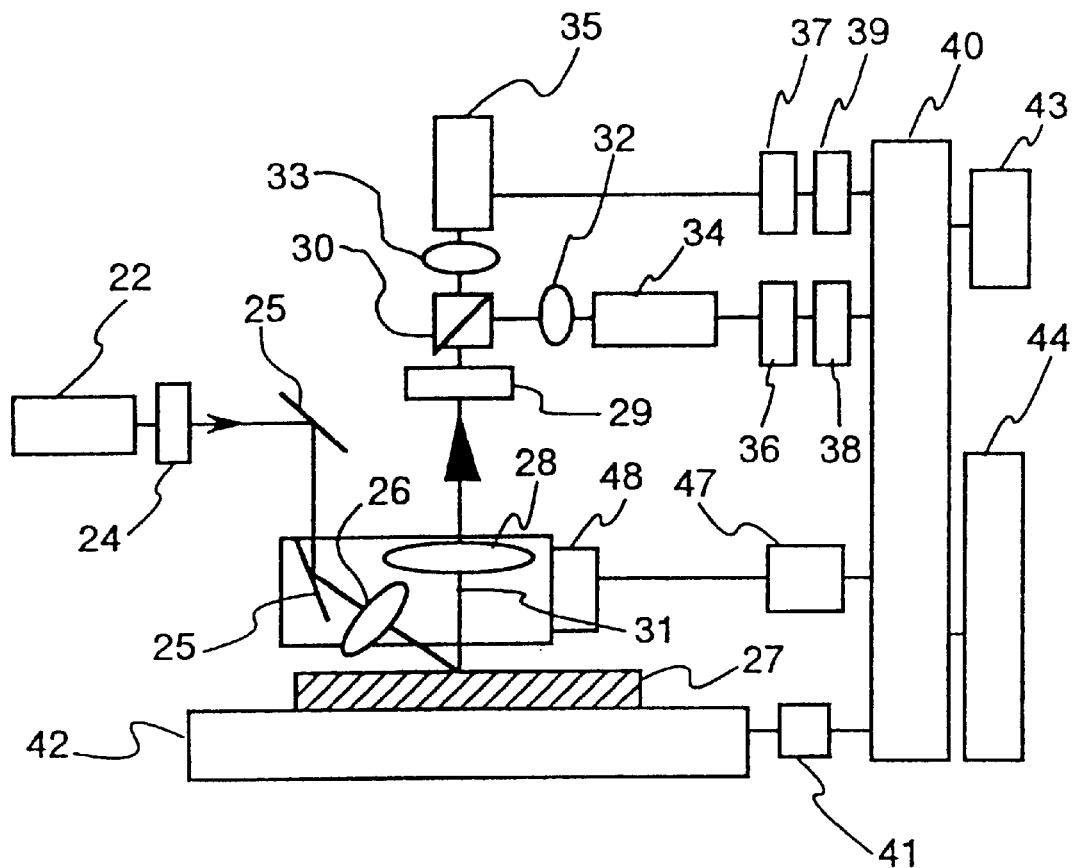
FIG. 16 is a schematic diagram of the construction of the embodiment 2 of the invention.
Figure 17:
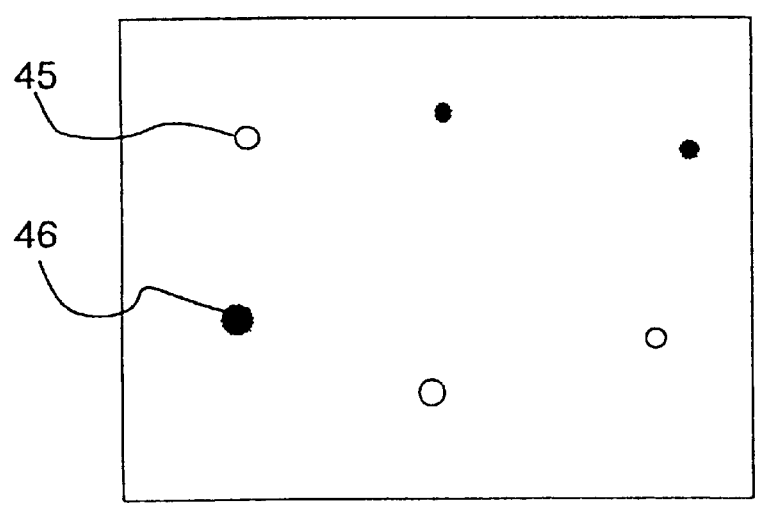
FIG. 17 shows the result of discriminating between the foreign particle on the crystal surface and the defect within the crystal and measuring them, according to the embodiment 2 of the invention.

This embodiment will be described with reference to FIG. 16. A linearly polarized YAG laser light beam 22 of 1.064 μm in wavelength is circularly polarized by a ¼ wavelength plate 24, reflected from mirrors 25 into a lens 26 by which it is focused, and then incident to a CZ type silicon wafer 27 at an angle of about 75°. As a result, a defect is detected of the oxide educt ($SiO_2$ particle) included within this wafer 27. A scattered light ray 31 from the defect is condensed by a lens 28 of NA, 0.4, and the fluorescence is eliminated by a filter 29. The scattered light 31 from the filter is incident to a polarization beam splitter 30, which then separates it into the scattered light components of which the electric vectors are respectively perpendicular and parallel to a plane (hereinafter, referred to as observation plane) that is formed by the optical axis for the radiated light and the optical axis for the detection of the scattered light. The separated polarized components are passed through lenses 32, 33, and fed to optical detectors 34, 35, which then detect the scattered light intensity Iv with its electric vector perpendicular to the observation plane and the scattered light intensity Ih parallel thereto, respectively. The detected signals are amplified by amplifiers 36, 37, and digitized by A/D converters 38, 39, respectively. While an XY stage 42 is being scanned in the XY directions by a driver under the control of a computer 40, the digitized scattered light intensities Iv, Ih are fed to the computer 40. The computer 40 calculates the polystyrene-converted particle diameter of each detected particle by Mie scattering theory from the signal Iv. The particles of 0.5 μm or below in diameter are discriminated to be foreign particles on the surface or internal defects by comparing the Iv and Ih values. The volume or diameter of the particle decided as a foreign particle on the surface is calculated on a polystyrene-conversion basis, and that of the particle decided as an internal defect is computed on a $SiO_2$-conversion basis. This value is displayed on a display 43 and printed out by a printer 44. FIG. 17 shows an example of the results of the discrimination between the foreign particle on the surface and the internal defect below the surface and the measurement of those particles and defects. In this figure, white circles 45 indicate defects within the crystal material with their size shown on a $SiO_2$-conversion basis, and black circles 46 indicate foreign particles on the crystal surface with their size indicated on a polystyrene-conversion basis. Here, when Ih/Iv<1, the detected particle was determined as a foreign particle on the surface, and when Ih/Iv>1, it was determined as a defect located within the crystal material. The sensitivity of the measuring system is previously determined by measuring the polystyrene standard particle of known diameter attached on the surface of a silicon wafer. During measurement, a piezo-electric element 48 is controlled by a driver 47 in order to maintain the wafer surface at a constant height. In place of the polarization beam splitter 30, a half mirror and a Gran Thompson prism or Thompson prism may be used to separate the polarized components of the scattered light. Also, in the construction of this embodiment, the incidence angle may be other than 75°. In that case, it is desirable that the optical system be arranged to detect the backward scattered light from the crystal defect and the 90°-directional scattered light from the foreign particle on the surface.

This embodiment has the same effect as the embodiment 1.

Embodiment 3

Figure 14:
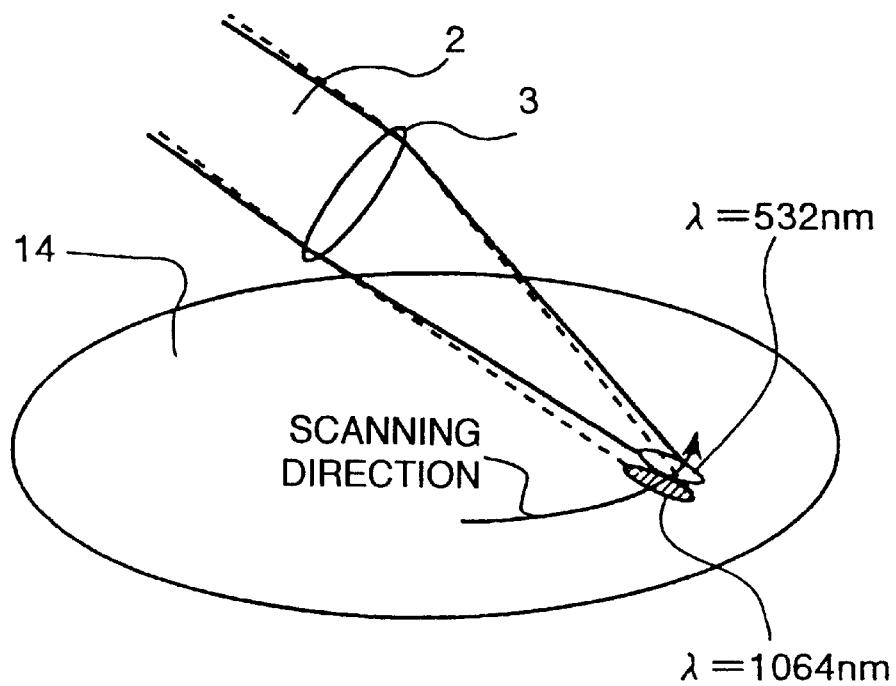
FIG. 14 shows an example of two different-wavelength light rays radiated slightly shifted in the scanning direction, according to the present invention.
Figure 18:
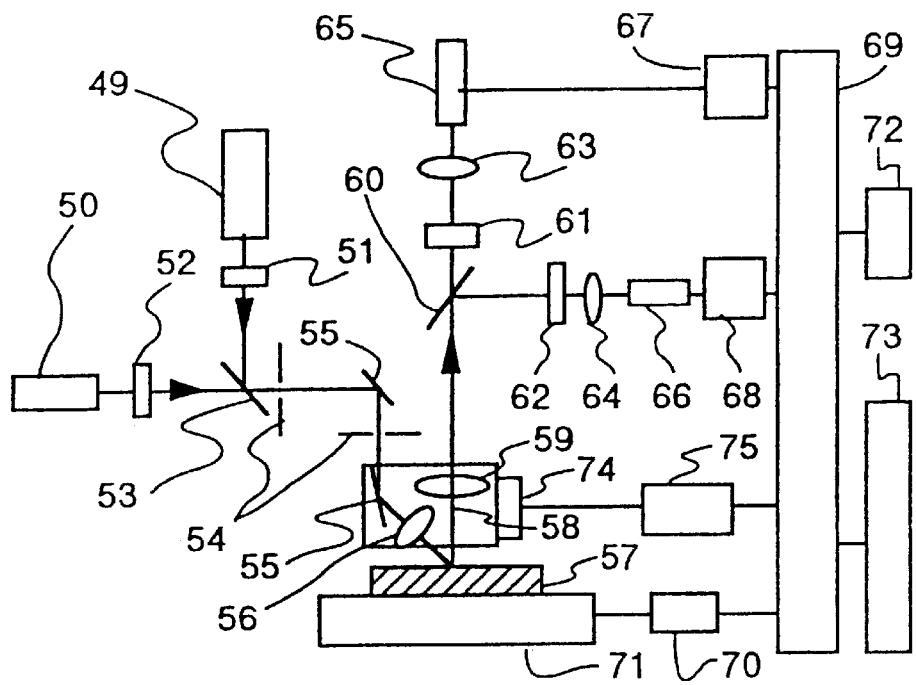
FIG. 18 is a schematic diagram of the construction of the third embodiment of the invention.

This embodiment will be described with reference to FIG. 18. A sample 57 is a silicon wafer. There are shown a 1064-nm wavelength YAG laser light source 49 and a second harmonic light (SHG) source 50 which generates the second harmonic of the beam from a 532-nm wavelength YAG laser. The light beams from those sources are passed through ½ wavelength plates 51, 52 so that their polarization directions can be adjusted relative to the plate surface being measured. Then, the light beams are added by a half mirror 53, passed through slits 54 for optical axis adjustment, reflected from mirrors 55, condensed by a lens 56, and incident to the silicon wafer 57. In this case, as shown in FIG. 14, the 1064-nm wavelength light is faster radiated on the defect than the 532-nm light while the scanning is being made. As the scattered light is detected during the scanning, the oxide educt ($SiO_2$ particle) included in the sample wafer is detected as a light scattering body. The scattered light, 58 from a defect as the light scattering body is condensed by a lens 59, and it is passed through and reflected from a half mirror 60. Then, only the wavelengths 1064 nm and 532 nm of the scattered light are selected by filters 61, 62. the scattered light rays 58 in both directions are respectively condensed by lenses 63, 64, detected by optical detectors 65, 66, and amplified by amplifiers 67, 68. The XY stage 71 is scanned in the XY directions by a driver 70 under the control of a computer 69, and the two scattered light intensities S1 (a wavelength of 1064 nm) and S2 (a wavelength of 532 nm) are sequentially fed to the computer 69. Here, the diameter d of each defect is computed on a $SiO_2$-conversion basis by Mie scattering theory from the scattered light intensity Si of the wavelength 1064 nm of the two kinds of data from each defect, the refractive Index 1.45 of $SiO_2$ to the wavelength 1064 nm, and the refractive index 3.56 (relative to the wavelength 1064 nm) of silicon (Si) as a medium. The ratio, $\sigma(532)/\sigma(1064)$ between the scattering cross-sectional areas of the $SiO_2$ particle of diameter d to the wavelengths 532 nm and 1064 nm is estimated by referring to a table of the scattering cross-sectional areas $\sigma$ and particle size d previously calculated by the scattering theory. On the other hand, the apparatus constants of C1 and C2 in Equation (5) are previously determined by measuring the polystyrene standard particle of known diameter attached on the surface of a silicon wafer. The depth of the defect from the surface is also determined by substituting these $\sigma(1064)$, $\sigma(532)$, $\sigma(532)$ $\sigma(1064)$, and the two different scattered light intensities S (1064), S (532) into Equation (5). Thus, the size and depth of each detect are derived, and the results are indicated on a display 72 and printed out by a printer 73. During the measurement, the height of the wafer is controlled to be within 2 μm by a servo mechanism using a piezo-electric element 74. In the above example, it is possible to use a cylindrical lens as the lens 56 by which the incident light can be condensed and radiated in a form of a flat cross-sectional shape, and use an array detector as the optical detectors for detecting the scattered light from the flat radiated region, with the scattered light from defects being received as data by the parallel array elements. In this case, the wafer measuring time can be decreased. In the above means, the condenser lens for irradiation is desired to have little chromatic aberration to wavelengths of 1064 nm and 532 nm. In addition, the same lens 56, which is used to supply the laser beam to the wafer 57 after the laser light beams are added by the half mirror 53, may be replaced by separate lenses to which the respective laser beams are incident. Moreover, the amplifiers 67, 68, which amplify the signals and supply them to the computer 69 where the depth Z is calculated by use of Equation (5), may be replaced by a logarithmic amplifier for amplifying the signals and a differential amplifier which produces the difference between the two signals and supplies the result to the computer where the depth Z is calculated, because Equation (5) can be rearranged by use of logarithmic formulas into the following equation.

$$Z=C1(ln(S1)-ln(S2)+ln(C2\sigma2/\sigma1)) \qquad (11)$$

At this time, it is possible to amplify one signal by the logarithmic amplifier, supply the result to the computer, and calculate the logarithm of the other signal not passed through the logarithmic amplifier and the depth Z from the difference between the values in the computer.

The object lens for condensing the scattered light is desired to have a much longer depth of field than the depth to which the incident light of wavelength λ2 enters into the crystal material. The reason for this will be described below. Here, it is assumed that the scattered light has been detected from the defect that is within the depth of field relative to light of wavelength λ1 but out of the depth of field relative to light of wavelength λ2. At this time, if the depth of field of the object lens is shorter than or substantially equal to the depth to which light of wavelength λ2 enters into the crystal material, the scattered light S2 to be measured will be smaller than that acquired when the defect is located within the depth of field. Thus, the ratio S1/S2 will be large, and the depth Z will be calculated to be larger than the actual value from Equation(5). In order to avoid this situation, the object lens for detection is required to have a loner depth of field than Γ2.

According to this embodiment, the depth at which a foreign particle or defect is located below the surface of a sample can be precisely measured with a resolution equivalent to the radiated wavelength or below, and the proper distribution of particle sizes can be derived. In addition, while the measurement of defects of silicon wafers is described in this embodiment, this embodiment may be applied to the measurement of foreign particles of the amorphous silicon layer in thin film transistors that are used in liquid crystal displays as described above.

Embodiment 4

Figure 19:
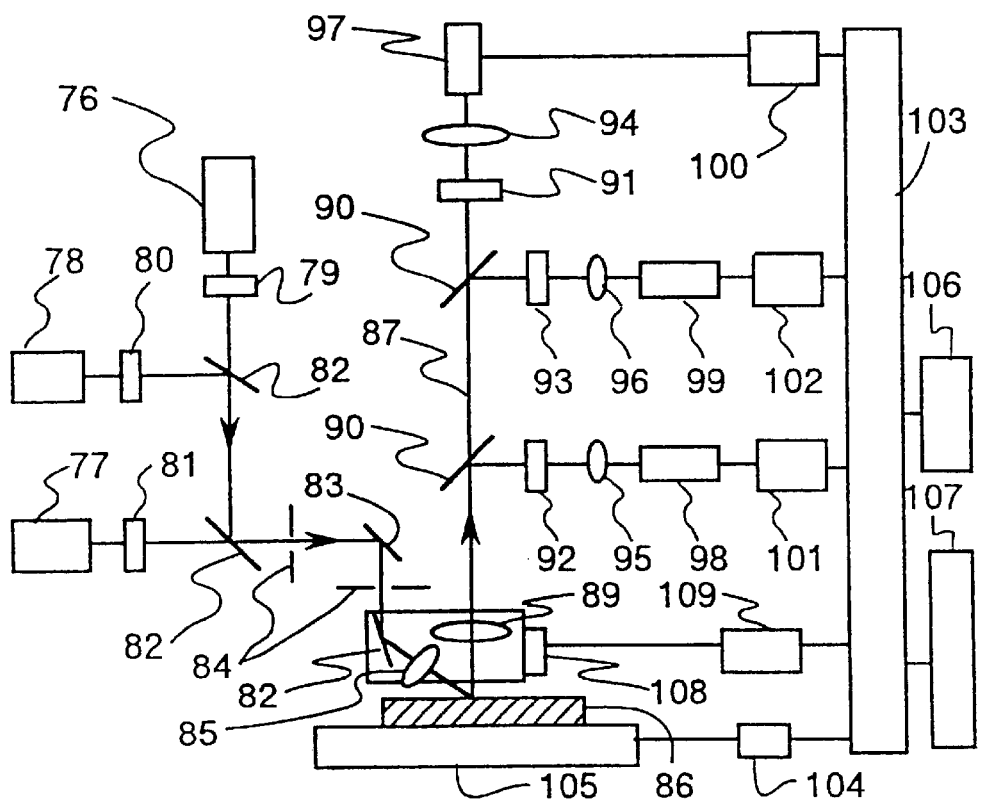
FIG. 19 is a schematic diagram of the construction of the fourth embodiment 4 of the invention.

This embodiment will be described with reference to FIG. 19. There are shown a YAG laser light source 76 of wavelength 1064 nm, a second harmonic (SHG) light source 77 for generating the second harmonic of YAG laser light of wavelength 532 nm, and an argon laser light source 78 of wavelength 488 nm. The light beams from those sources are passed through ½ wavelength plates 79, 80 and 81 so that their polarized directions are adjusted relative to the surface of a crystal material being measured. Then, these light beams are added by half mirrors 82, passed through slits 84 for optical axis adjustment and through a mirror 83, and condensed by a lens 85 onto a CZ silicon wafer 90.

The oxygen precipitates ($SiO_2$) included in this wafer can be detected as defects. The scattered light, 87 from the defect is condensed by a lens 89, and passed through and reflected from half mirrors 90. The scattered light rays from those mirrors are passed through filters 91, 92, 93 so that only the wavelengths of 1064 μm, 532 nm and 488 nm are selected, respectively. After fluorescence Is removed by the filters 91, 92, 93, the scattered light rays 87 are condensed by lenses 94, 95, 96, detected by optical detectors 97, 98, 99, and amplified by amplifiers 100, 103, 102. While an XY stage 105 is being scanned in the XY directions by a driver 104 under the control of a computer 103, the three different scattered light intensities S1 (wavelength, 1064 nm), S2 (wavelength, 532 nm), S3 (wavelength, 488 nm) are supplied to the computer 103. Here, the size of the defect is computed by Mie scattering theory using the scattered 1064-nm wavelength light intensity S1 of the three kinds of data on each defect, and the refractive index 1.45 of $SiO_2$ to the wavelength 1064 nm. The ratio, σ2/σ1 of the $SiO_2$ particle of diameter d relative to wavelengths 532 nm and 1064 nm is estimated by referring to a table of scattering cross-sectional area σ and diameter d previously calculated by the scattering theory. Similarly, the scattering cross-sectional area σ3 to wavelength 488 nm is computed, and the ratio, σ3/σ1 is estimated for each defect. As is similar to the embodiment 3, the apparatus constants C1, C2 are previously determined, and the depth at which the defect is located within the wafer is determined by use of these C1 and C2, the three different scattered light intensities S1, S2, S3, Equation (5), and the ratios, σ2/σ1 and σ3/σ1. In this case, the depth resolution is increased in the region shallower than a depth of 3.5 μm as compared with the case in which the depth is determined by use of only the ratio S2/S1 as in the embodiments 1 and 3. Thus, the size and depth of each defect are derived, and the results are indicated on a display 106 and printed out by a printer 107. During the measurement, the height of the wafer surface is controlled to be within 2 μm by a servo mechanism 109 using a piezoelectric element 108. A cylindrical lens may be used in place of the lens for condensing the incident light, and an array detector may be used in place of the optical detector for detecting the scattered light. In addition, the same lens 85 by which the laser light rays added through the half mirror 82 are condensed onto the wafer 86 may be replaced by separate lenses by which the light rays are condensed onto the sample without adding those rays. The third wavelength in this embodiment may be argon laser beam of a shorter wavelength, for example, 458 nm in place of 488 nm.

This embodiment has the same effect as the embodiment 3.

Embodiment 5

Figure 20:
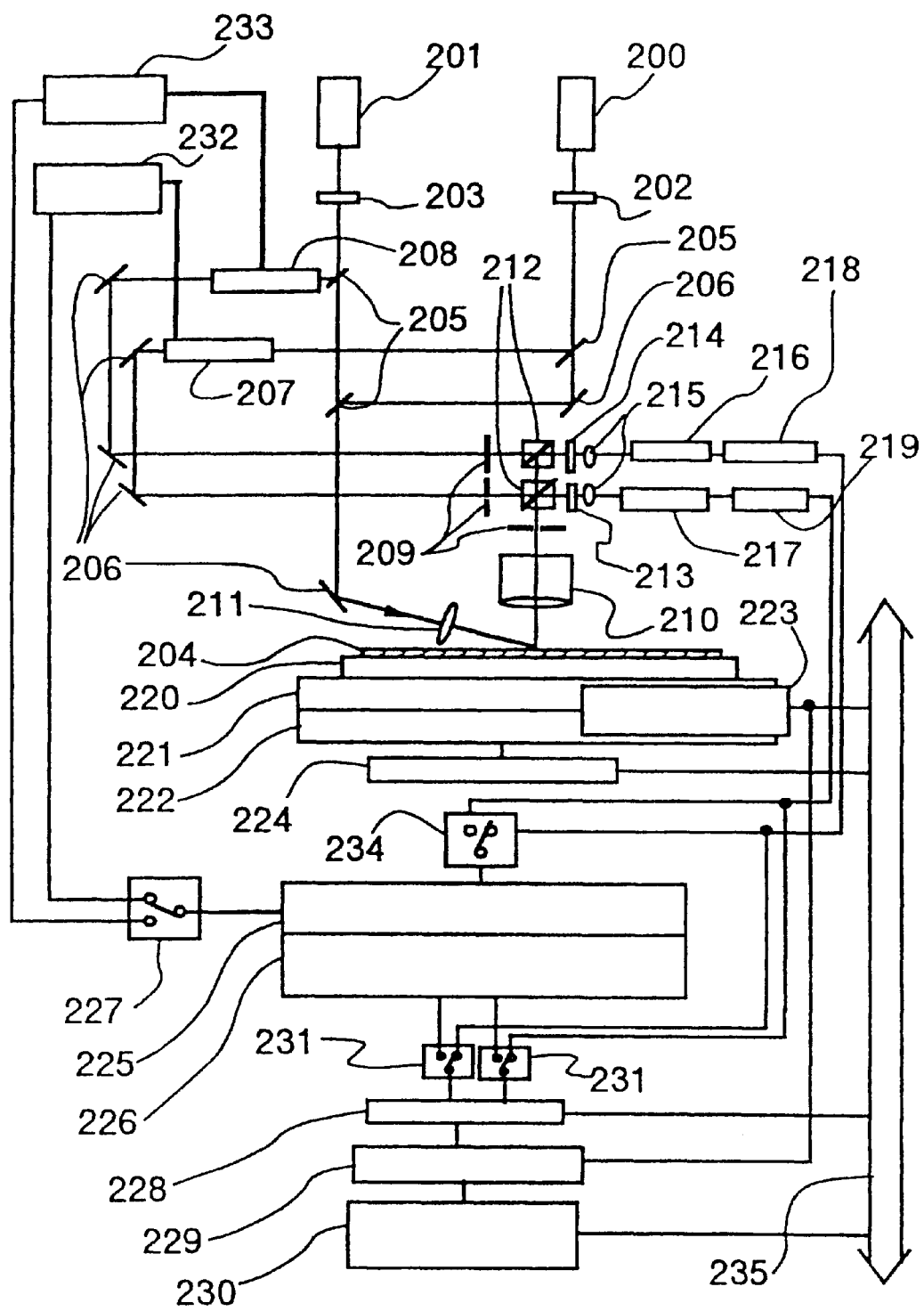
FIG. 20 s a schematic diagram of the construction of the fifth embodiment 5 of the invention.

This embodiment will be described with reference to FIG. 20. There are shown a YAG laser light source 200 of wavelength 1064 nm, and a second harmonic (SHG) light source 201 for generating the second harmonic of YAG laser light of wavelength 532 nm. The light beams from those sources are passed through ½ wavelength plates 202, 203 so that their polarization directions are adjusted relative to the surface of a crystal material (sample wafer) 204. Those laser beams are passed through and reflected from half mirrors 205, and then parts of the laser beams are added by half mirrors 206 and condensed by a lens 211 onto the surface of the sample wafer 204. The other parts reflected from the half mirror 205 are passed through AO modulators (modulation frequency: 20 MHz) 207, 208, and openings 209 to serve as reference light. The scattered light from the sample is condensed by an object lens 210. The scattered light from a defect after being condensed by the object lens 210, and the reference light are passed through half prisms 212, wavelength selecting filters 312, 214 and a lens 215 and entered into a detector (the wavelength 532 μm to a photoelectric multiplier 216, the wavelength 1064 nm to a photodiode 217). The detector is followed by amplifiers 218, 219. The measurement is made by detecting the scattered light while the sample is being scanned. The sample wafer 204 is fastened to a rotating stage 221 by a vacuum chuck 220, and it is moved outward together with an X-axis stage 222 in the radius direction from the rotation center at a constant speed while it is being rotated, so that the entire surface or part of the sample wafer can be scanned. These stages are controlled by a scanning control driver 223 formed of a rotary encoder and linear encoder and a stage driver 224. The scattered light from a defect within the wafer is detected as a pulse with respect to time while the scanning is made. As the wavelength selecting filters, the filter 214 for eliminating longer wavelengths than 550 nm is used for the 532-nm light, and the band-pass filter 213 for wavelength 1064 nm is used for the 1064-nm wavelength light.

The measurement mode includes two different modes of direct detection mode and heterodyne detection mode. In the latter heterodyne detection mode, the interference beat of 20 MHz is detected by the detector, and the signals of the respective wavelengths are alternately switched by a change-over switch 227 for AOM drivers 232, 233 and a change-over switch 234 for the detection system, amplified by a lock-in extender 225 (for extending the band of a lock-in amplifier 226 to over 20 MHz) and the lock-in amplifier 226, digitized by an A/D converter 228, stored in a memory 229, and later transferred to a computer 230. In the direct detection mode, the reference light is cut off, the scattered light from a defect is detected by a direct detector. In this mode, the signal is not passed through the lock-in extender 225 and lock-in amplifier 226, but it is digitized by the A/D converter 228, stored in the memory 229, and later transferred to the computer 230. The heterodyne detection mode and the direct detection mode are switched by a signal change-over switch 231. In this case, the reference light is cut off by inserting a light-shielding plate or the like.

Figure 21:
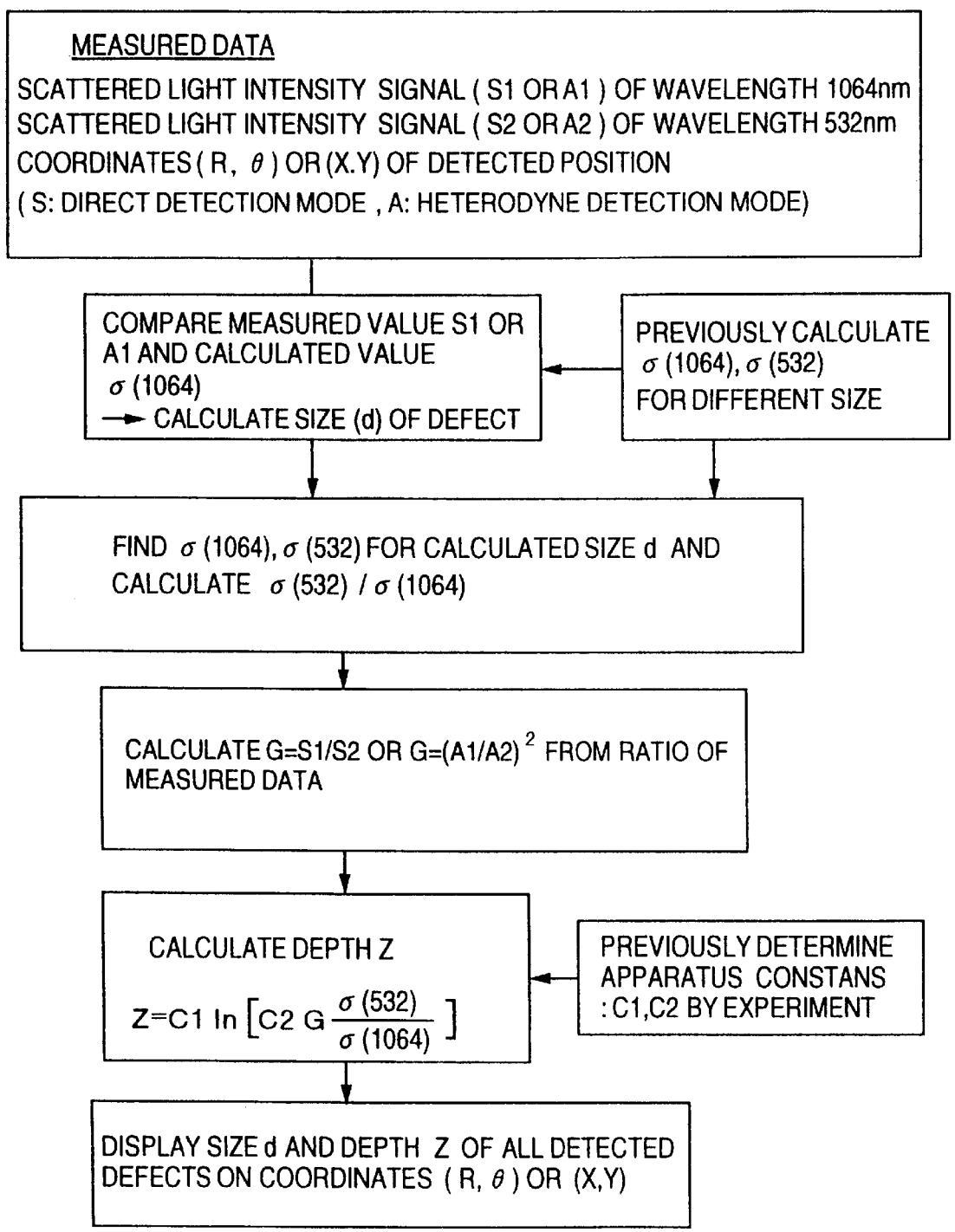
FIG. 21 is a flowchart for the measured data analyzing method according to the embodiment 5 of the invention.

The measured data is analyzed as shown in FIG. 21. That is, in the heterodyne detection mode, the measured data includes a scattered light amplitude signal of each wavelength, and detected position coordinates (the distance R from the rotation center is obtained by the linear encoder for the X-axis stage, and the rotation angle θ by the rotary encoder). The particle diameter d is estimated on a $SiO_2$ conversion basis by use of the 1064-nm wavelength scattered light amplitude signal of the measured data, and a table of particle size vs.scattering cross-sectional area which is previously produced. In addition, the ratio, σ (1064)/σ (532), between the scattering cross-sectional areas σ (1064), σ (532) of $SiO_2$ particle of diameter d to wavelengths 1064 nm, 532 nm is also estimated by referring to the table (particle diameter vs. scattering cross-sectional areas to the wavelengths 1064 nm, 532 nm). Then, the ratio between the two-wavelength scattered light amplitudes of measured data is calculated, and G is determined. In addition, the depth Z is estimated by use of the previously determined apparatus constants C1 and C2 as in the above embodiments and according to the flowchart shown in FIG. 21. The distribution (depth distribution, and particle size distribution) of crystal defects within the wafer is transferred through a control data bus line 235 to the display and printer, where it is displayed and printed out.

The apparatus arrangement of this embodiment is capable of making higher-sensitivity measurement than in the embodiments 3 and 4.

Embodiment 6

Figure 22:
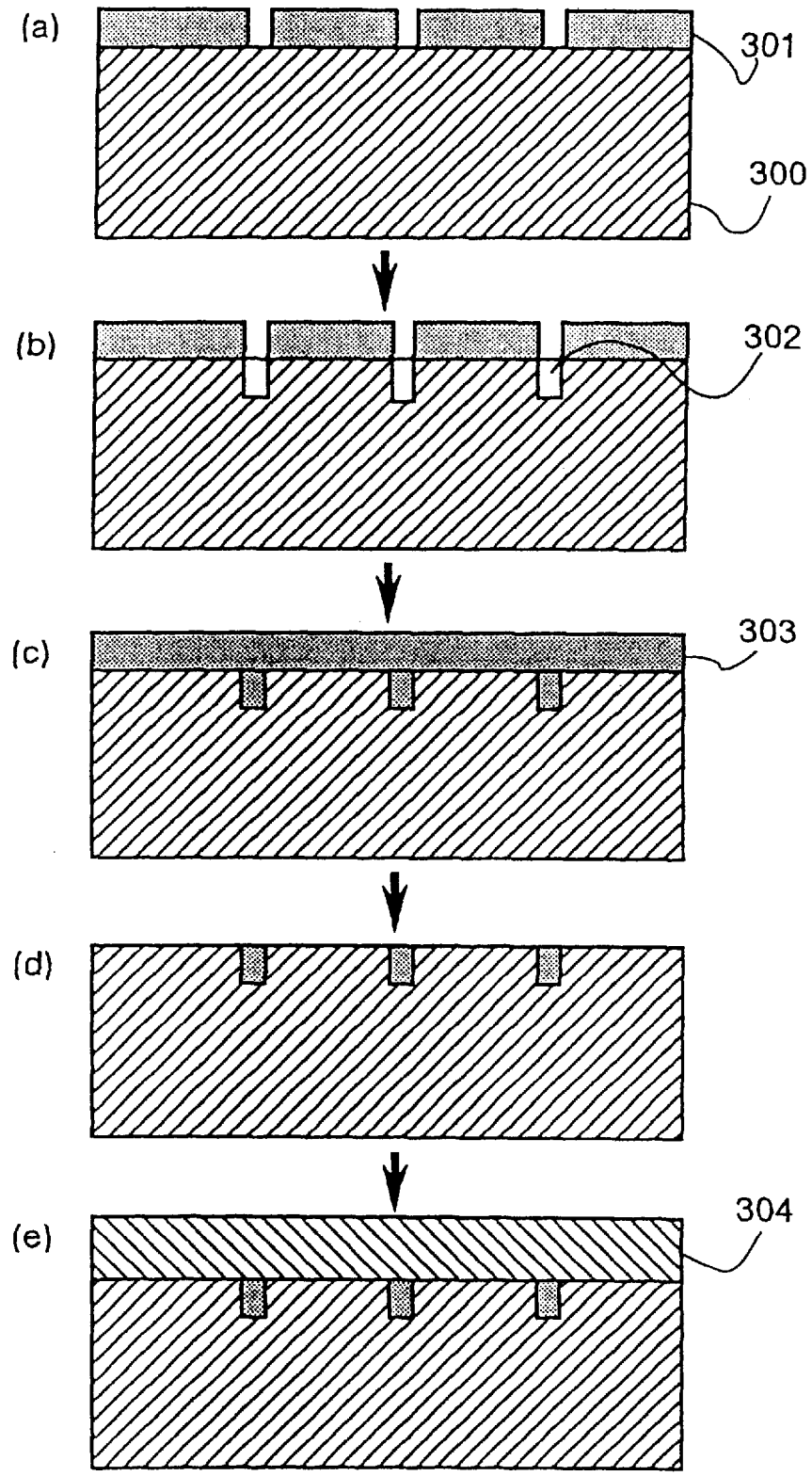
FIG. 22 is a flow diagram showing one example of the standard sample producing process according to the embodiment 6 of the invention.

The crystal defect measuring apparatus is corrected by measuring the standard particle produced as described later, and adjusting the size and depth (particularly, in the near-surface region) of the defect to meet the specifications of the standard sample. One example of the standard sample producing method will be described first with reference to FIG. 22. Since the FZ type silicon crystal includes little oxide educt, it is recommended to use for a standard sample substrate 300. A photo resist 301 is coated on the FZ silicon crystal substrate 300, and a dot pattern of 0.5-μm diameter is drawn on the surface by an electron beam drawing apparatus ((a)). The spacing of the dot pattern is desired to be wider than the size of the region to be detected at the time of measurement. The reason for this is that when it is narrower than that size, two particles or more can be included within the detected region, thus disabling the standard particle from serving as a size standard. Holes (deep grooves) 302 are formed 0.5 μm deep in the silicon substrate by plasma etching ((b)). After the resist 301 is selectively removed, an oxide film 303 is grown on the silicon surface by chemical vapor deposition (CVD) ((c)), and then this film is selectively removed by plasma etching. In that case, when the etching is stopped just after removing the silicon oxide film on the flat surface other than the deep grooves 302, $SiO_2$ remains not removed from the deep grooves 302 ((d)). Thus, the depth of the deep grooves 302 is decreased to a desired value by adjusting the amount of the etching. Then, an amorphous silicon film 304 of a desired thickness is formed on the surface by CVD ((e)). The film thickness is adjusted to be in the order of 1 μm to 10 μm by setting the depositing time and speed. The film deposition should be made at a temperature of, preferably 550° C. or below in order to prevent the film from being crystallized during the process. Since the film growing speed is reduced at such a low temperature, a high-order silane ($Si_nH_{2(n+1)}$, n is an integer) such as disilane ($Si_2H_6$) is preferably selected as a reaction gas in place of monosilane ($SiH_4$) which is usually used, in order to prevent the reduction of growing speed. The amorphous silicon film can be formed by sputtering other than CVD. In addition, the CVD utilizing plasma discharge is advantageous in that it can deposit amorphous silicon films at a temperature of 300° C. or below with a speed equivalent to or higher than in the normal CVD. In this embodiment, the amorphous silicon is formed for the following reason. That is, when other thin films, for example, a silicon film formed by epitaxial growth is used, this film which is crystallized has dislocations, stacking faults and so on caused by $SiO_2$ particles formed within the grooves, thus often interfering with the measurement. However, when the formed $SiO_2$ particles are large, and when the dislocations and stacking faults can be distinguished from the $SiO_2$ particle and measured, the presence of dislocations and stacking faults constitutes no obstacle to the measurement, and thus the silicon thin film can be epitaxially grown and used. In this case, there is the advantage that the optical constant of the silicon thin film present on the $SiO_2$ particle is approximately equal to the value of monocrystalline silicon substrates. Also, polycrystalline thin films formed by CVD can be used in addition to the epitaxially grown silicon thin film. Moreover, after being formed, the silicon film can be damaged by ion implanting or the like so as to be amorphous. However, if, now, we consider the acceleration voltage in the ion implanting apparatus that is available from the industrial standpoint, this method is often effective when the silicon thin film is about 1 μm or below in thickness.

Figure 23:
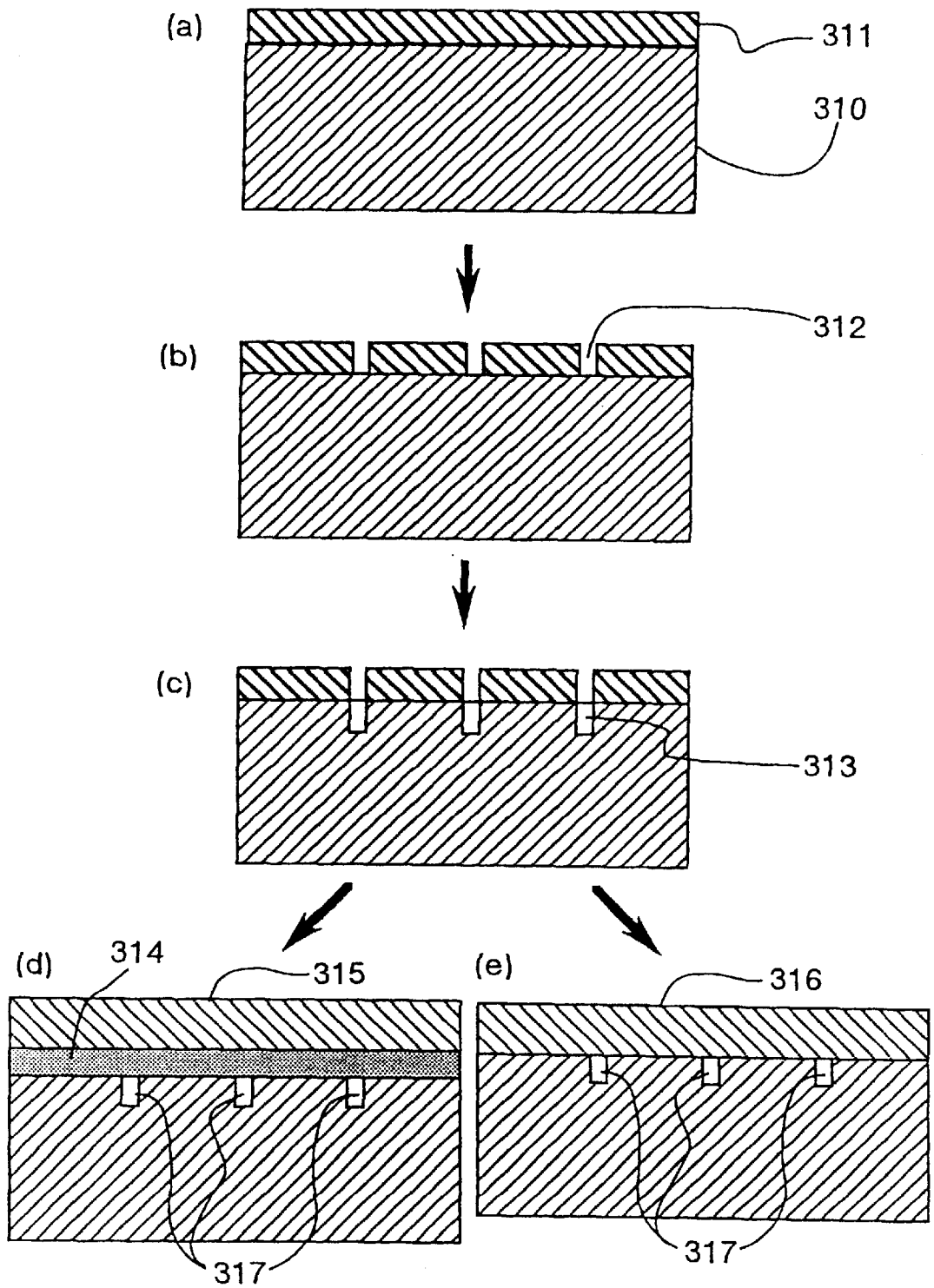
FIG. 23 is a flow diagram showing another example of the standard sample producing process according to the embodiment 6 of the invention.

FIG. 23 shows another example of the production of the standard sample. First, a resist 311 is coated on an FZ silicon crystal substrate or a silicon crystal substrate 310 with at least a silicon thin film epitaxially grown on the surface to a thickness of 1 μm or above ((a)), a dot pattern 312 is formed in the coating by an electron beam drawing apparatus ((b)), and holes 313 are formed to a constant depth in the silicon by plasma etching ((c)). After the resist is removed, the substrate is covered with a silicon wafer 315 which has a silicon oxide film 314 of 50-nm thickness or below formed on its underside ((d)) or the substrate is covered directly with a silicon wafer 316 ((e)). This covering technique is described in Japanese Patent Publication JP-B-39-178679 or Journal of Appl. Phys. Letter., published in 1975, vol. 48, page 78. Thus, holes of a constant size can be formed in the silicon at a constant depth from the surface. According to this process, cavities 317 are formed within the silicon substrate in place of the dummy defects of $SiO_2$ shown in FIG. 22, and thus dummy defects having a refractive index of 1.0 can be formed in the substrate.

In the above process, the size of dummy defects produced can be controlled by changing the diameter of dots drawn in the resist and the etching depth in the silicon, and the depth at which the dummy defects are located below the surface of the substrate can be controlled by changing the thickness of the silicon layer formed on the surface.

The crystal defect measuring apparatus can be corrected by measuring the standard particles according to the invention on the apparatus for measuring crystal defects, and adjusting the defect size and depth to meet the specifications of the standard sample. However, the standard sample with the cavities as dummy defects is required to be corrected for the detected signal intensity due to the difference between their refractive index and that of $SiO_2$ particles.

Embodiment 7

This embodiment of the invention will be described with reference to FIGS. 24, 25 and 26. The present invention can be effectively used in the quality control and process management of semiconductor production line.

Figure 24:
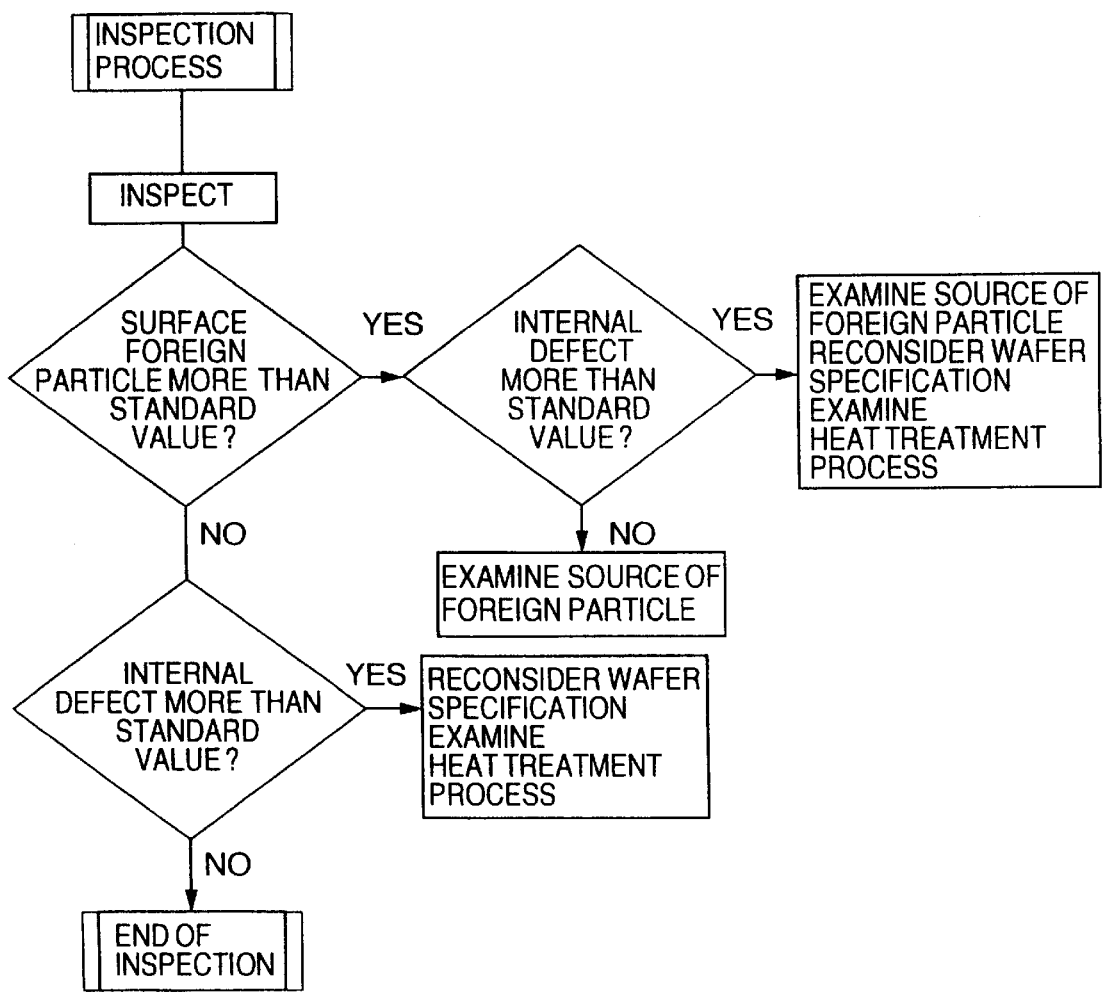
FIG. 24 is a flowchart for the quality control of silicon wafers according to the embodiment 7 of the invention.

FIG. 24 is a general flowchart of the quality control to which the invention is applied. The inspection apparatus of the invention is capable of nondestructive, contactless inspection, and hence can make not only sampling inspection but also total inspection. In addition, while it is desirable to inspect the entire surface of the wafer, only a particular region on the wafer may be measured for the reduction of inspecting time. When each of foreign particle on the surface and internal defects is out of the range of certain standard values, a countermeasure for each defect is necessary. If the number of foreign particles exceeds a standard value, the source of the foreign particles should be examined, and it is necessary to suppress the generation of foreign particles. If the internal defects are out of the range of standard values, the specification of the wafer must be reconsidered or the heat treatment process is required to be more considered.

Figure 25:
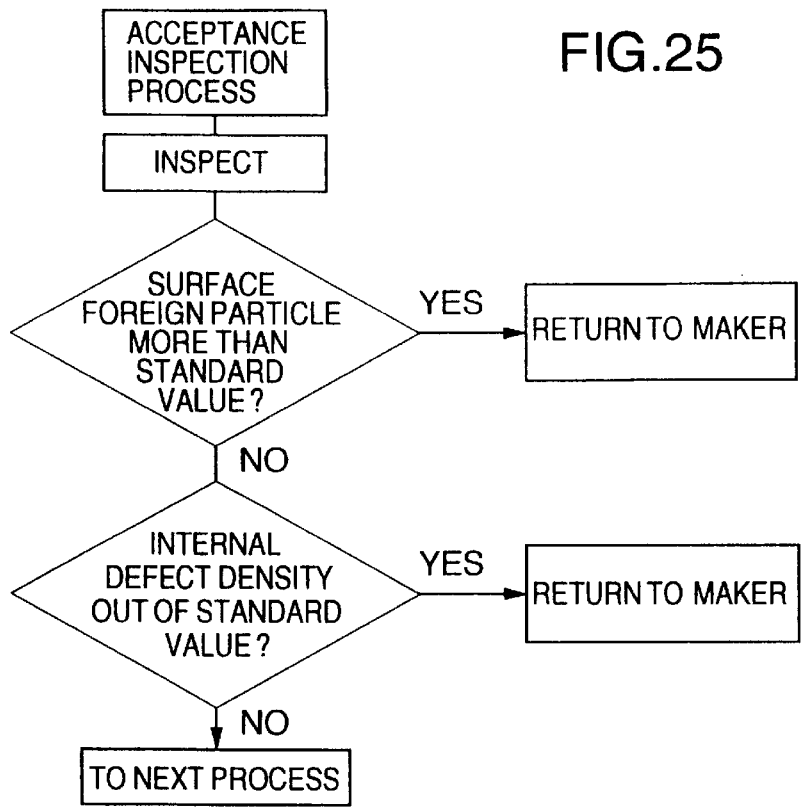
FIG. 25 is a flowchart for the silicon wafer acceptance inspection according to the embodiment 7 of the invention.

FIG. 25 is a flowchart of acceptance inspection. If the number of foreign particles on the surface exceeds the standard value, it will be considered that the foreign particles were probably generated in the wafer maker, and hence you should return the wafers to the maker, and request the maker to take a measure to cope with that situation. If the density of internal defects is out of the standard value, the defects were probably generated on the wafer maker side, and thus you should return them to the maker, and request the maker to take a measure. In either case, since the cause of the defects can be found by distinguishing between the foreign particle and the internal defect, and measuring them, the wafer maker can easily take a measure. The semiconductor manufacturer can also easily take a measure against the defective products by grasping the density of external particles and internal defects just after the acceptance inspection.

Figure 26:
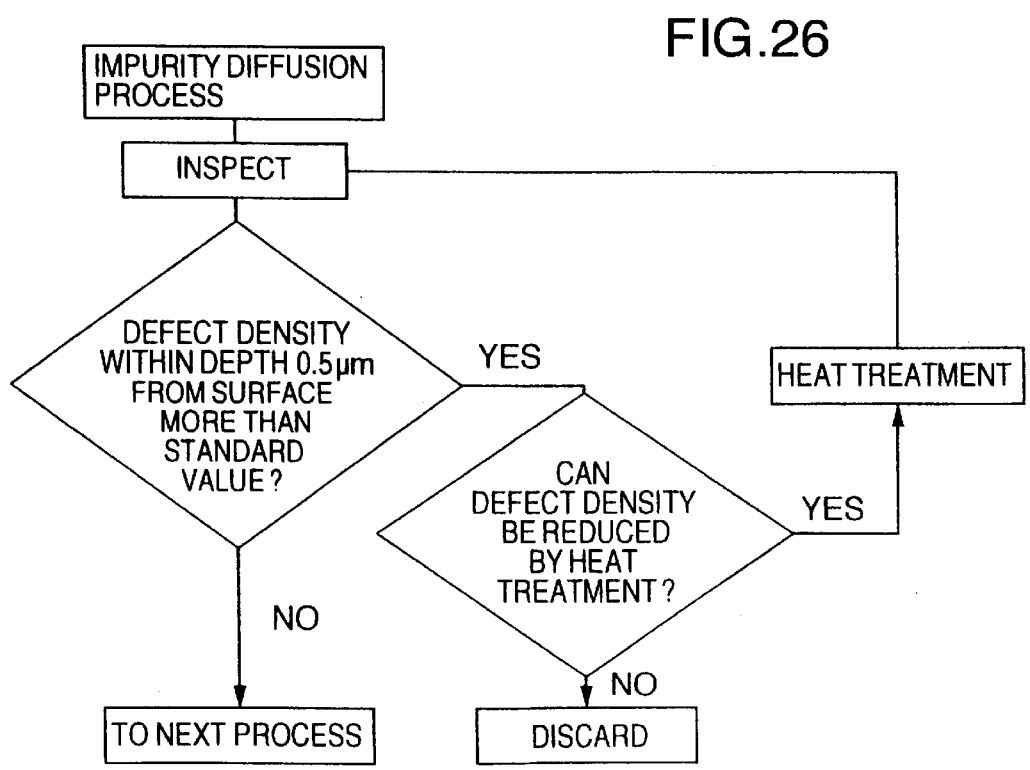
FIG. 26 is a flowchart for the inspection after the heat treatment for the silicon wafer impurity diffusion according to the embodiment 7 of the invention.

FIG. 26 is a flowchart of the inspection after the impurity diffusion heat treatment process following the ion implantation process. The DZ layer with almost no defect on the surface is formed by the impurity diffusion heat treatment process. However, if defects are present in the device making region (within a depth of 0.5 $\mu$m from the surface), the device built up in this region will be defective. Some defects can be extinguished by proper heat treatment. If it is found that the defect density can be reduced by heat treatment, the wafer with defects is heated, and returned to the production line, where it is again inspected. If it is found from the result of the inspection that the defect density is reduced to within the standard value, this product is treated as good product on the line, or it can be operated as a non-defective device. If it is found that the defects cannot be extinguished, the wafer is discarded at this stage, thus the cost in the following processes being reduced.

Embodiment 8

Figure 27:
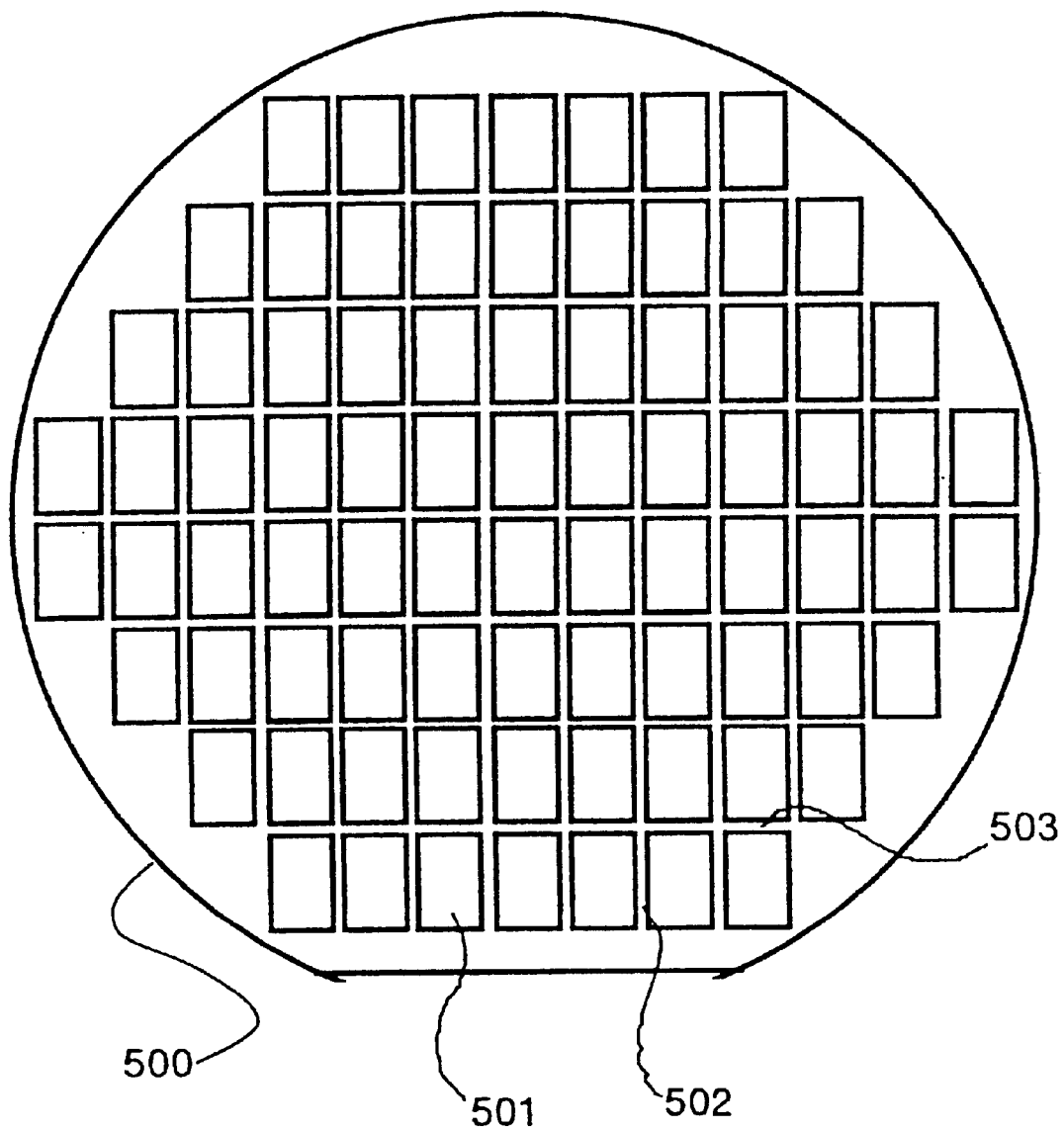
FIG. 27 shows a silicon wafer with LSIs formed.
Figure 28:
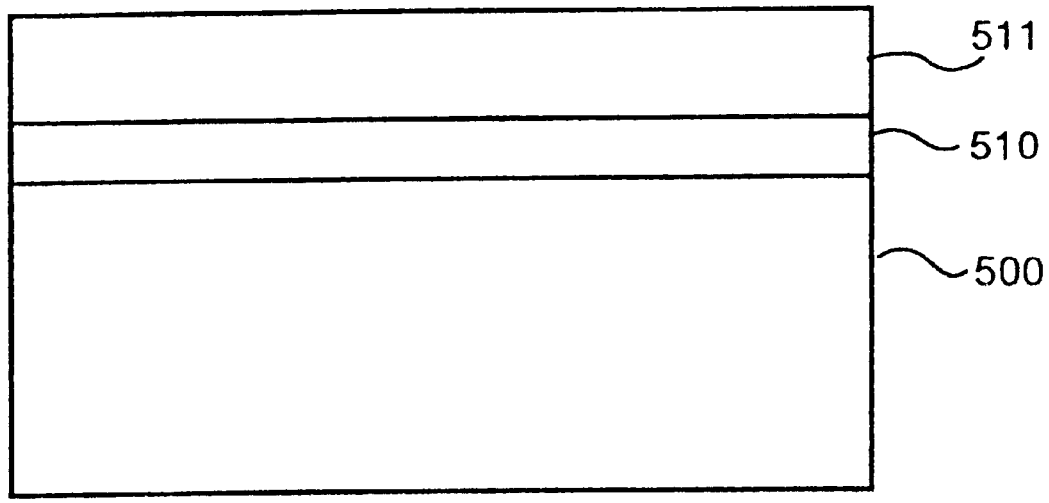
FIG. 28 is a cross-sectional diagram of the scribe region of the conventional silicon wafer.
Figure 29:
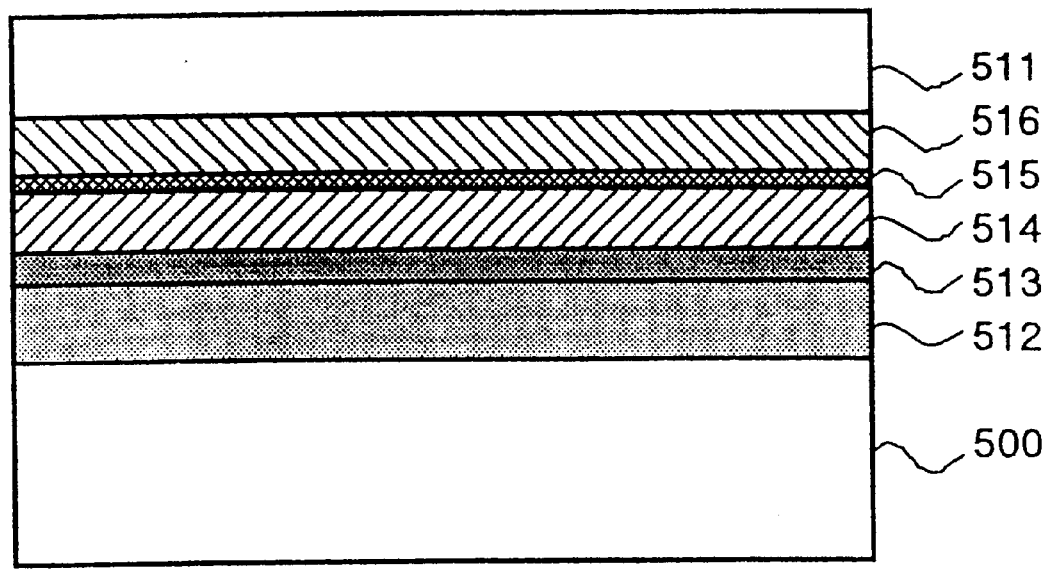
FIG. 29 is a cross-sectional diagram of the scribe region of a silicon wafer according to the embodiment 8 of the invention.

This embodiment will be described in detail with reference to FIGS. 27 to 29. As shown in FIG. 27. LSIs 501 are normally built up on a semiconductor substrate 500 in a matrix shape. The regions 502, 503 between the LSIs serve as tabs for cutting (scribe regions) when the substrate is cut along these regions into individual LSIs after the LSIs are completed. These regions have formed therein various different devices for evaluating the characteristics of the LSIs and a pattern for the alignment purpose in the lithography. As illustrated in FIG. 28, a thick silicon oxide film 510 (usually called field oxide film) is formed in order to electrically insulate between these devices. In this invention, the same structure (see FIG. 29) as the junction in DRAM is formed in at least part of the scribe regions of the semiconductor substrate in which DRAMs are built up. In other words, this structure has a depletion layer 512, a diffusion layer 513, an accumulation electrode 514, a capacitor insulating film 515, a plate electrode 516, and an interlayer insulating film 511. The accumulation electrode 514 and plate electrode 516 are made of a material of polycrystalline silicon. Under this construction, the scribe regions of the semiconductor substrate have formed therein defects of substantially the same kind and number (density distribution) as the junction in DRAM. In a sequence of processes for producing the DRAM, the crystal defects present in the scribe regions of the semiconductor substrate are suitably measured by the crystal defect measuring apparatus given in the embodiment 1. At this time, defects are measured at least in the region within a depth of 1 $\mu$m from the surface (if a thin film is formed on the substrate, the surface indicates the interface between the silicon substrate and the thin film) of the silicon substrate 500, and treated as being different from the external foreign particle. The density of the defects in the region 1 $\mu$m or below deep is determined on the basis of the results. If the density exceeds the management standard, the cause is examined by detailed analysis, and a necessary measure is taken. In addition, the sizes of the external particles and the density distribution over the surface is estimated. If it exceeds the management standard, a countermeasure is also taken to reduce the external foreign particles. Thus, the obstacles which cause problems can be extracted before the LSIs are completed, with the result that the loss due to defects can be reduced. Moreover, it is possible to reduce the possibility of problems such as delay of delivery date to the customer. Since the measurement according to the invention is nondestructive, and does not contaminate the semiconductor substrate, the samples can be again returned to the production process after the measurement, and continued to be complete as LSIs, thus waste being avoided.

This embodiment has the following advantages. Even after the completion of DRAMs, unsatisfactorily refreshed state can be grasped without a complicated and expensive apparatus such as the LSI tester. Particularly, even though the DRAM is not properly operated because of a certain unsatisfactory situation in the production process, the unsatisfactorily refreshed state can be understood. While in this embodiment the wiring conductor layers to be formed in the process following the plate electrode process are not formed in the scribe regions, the metal or metal compound of which the wiring conductor layers are made shuts out infrared light, thus interfering with the observation of defects within the semiconductor substrate by the crystal defect measuring apparatus. On the other hand, even though the polycrystalline silicon is heavily doped to be conductive as in this embodiment, it is transparent to infrared light if its total thickness is 1 $\mu$m or below, thus making it possible to observe the defects within the semiconductor substrate.

Even though the junction structure is formed in the region other than the scribe region, for example, in the region in which the electrodes (bonding pads) for drawing out external wiring conductors are formed, the defects within the semiconductor substrate can be observed by the crystal defect measuring apparatus using infrared light before the substrate arrives at the wiring conductor layer process stage. Similarly, the defects within the semiconductor substrate can be observed by use of devices produced for the evaluation of junction characteristics.

In addition, even though the above junction structure is not formed, it is effective to measure the crystal defects within the silicon substrate in the region in which no junction is formed, if necessary. Particularly, by measuring the oxide educts within the silicon substrate, and reflecting the results in the silicon crystal pulling condition and the heat treatment condition of the manufacturing process, it is possible to effectively control the contaminant gettering capability. For the reflection in the heat treatment condition, when the density of educts is smaller than the management standard, the heat treatment process is further added or the head treatment in the following stages is made at higher temperatures or for a longer time. If the density of educts is larger than the management standard, the reverse is performed.

While this embodiment is concerned with DRAM, this invention can be, of course, applied to other memory LSIs such as flash memories, microprocessors, and LSIs for particular use. Moreover, the present invention can be applied to the semiconductor devices other than silicon, such as GaAs-IC and semiconductor lasers.

We claim:

1. An inspection method for measuring a location of a foreign particle on a surface of a sample and a location of a defect in said sample by utilizing a difference between a first scattered light ray from said foreign particle and a second scattered light ray from said defect when light is radiated to said sample;
   wherein said foreign particle and said defect are discriminated from each other by utilizing an angle difference between said first scattered light ray and said second scattered light ray.

2. An inspection method according to claim 1, wherein said light radiated to said sample is a single light.

3. An inspection method for measuring a location of a foreign particle on a surface sample and a location of a defect in a sample by utilizing a difference between a first scattered light ray from said foreign particle on said surface of said sample and a second scattered light ray from said defect in said sample when light is radiated to said sample;
   wherein said foreign particle on said surface and said defect are discriminated from each other by utilizing a polarizability difference between said first scattered light ray and second scattered light ray.

4. An inspection method according to claim 3, wherein said light radiated to said sample is a single light.

5. An inspection method for measuring a depth of a defect in a sample by utilizing a difference between a first and a second scattered light ray from said defect in said sample when a first light ray of a first wavelength and a second light ray of a second wavelength are radiated to said sample;
   wherein the depth at which said defect is located in said sample is measured by utilizing an intensity difference between said first scattered light ray of said first wavelength and said second scattered light ray of said second wavelength.

6. An inspection method according to claim 5, wherein said first and second wavelengths have different attenuation rates.

7. An inspection apparatus for measuring a location of a foreign particle and the location of a defect in a sample comprising:
   a light source unit;
   a stage for supporting a sample;
   a first optical system that causes light emitted from said light source unit to be irradiated to said sample;
   a second optical system that condenses the light scattered from said sample;
   means for separating said condensed light into a plurality of light rays in different light paths;
   a plurality of detectors for detecting said light rays that are separated in different light paths; and
   means connected to said plurality of detectors and for computing ratios between the detected intensities of a plurality of light signals, said first and second optical systems having optical axes thereof forming an angle of 50° to 120° relative to each other;
   wherein said first and second optical systems have the optical axes thereof forming different angles relative to the normal to the surface of said sample.

8. An inspection apparatus according to claim 7, wherein said separating means separates said condensed light into polarized components that are respectively perpendicular and parallel to a plane formed by the optical axes of said first optical system and said second optical system.

9. An inspection apparatus according to claim 7, wherein said light source unit is formed of light sources which respectively emit light of different wavelengths, and said separating means separates said condensed light into light of different wavelengths.

10. An inspection apparatus according to claim 7, wherein said light source unit is formed of light sources which respectively emit light of different wavelengths, and at least two of said plurality of different light sources have wavelength-selecting filters of different bandpass characteristics, respectively.

11. A semiconductor-device producing method including an inspection process in which light is radiated on the surface of a semiconductor wafer, so that a particle on said surface of said semiconductor wafer and a defect in said semiconductor wafer are inspected by utilizing a difference between a first scattered light ray coming back from said particle and a second scattered light ray coming back from said defect when said light is radiated on said surface.

12. A semiconductor-device producing method according to claim 11, wherein said inspection process separately detects a polarized component of said first scattered light ray from said particle and a second polarized component of said second scattered light ray from said defect.

13. A semiconductor-device producing method according to claim 11, wherein said light radiated to said sample is a single light.

14. A semiconductor-device producing method including an inspection Process in which a first light ray having a first wavelength and a second light ray having a second wavelength different from each other are radiated on said semiconductor wafer, so that a depth and a size of a defect in said semiconductor wafer are inspected by utilizing a difference between a first scattered light of said first light ray and a second scattered light of said second light ray.

15. An inspection apparatus for measuring a location of a foreign particle and the location of a defect in a semiconductor material comprising:
   a light source;
   a stage for supporting said semiconductor material;
   a first optical system that causes light emitted from said light source unit to be irradiated to said semiconductor material;
   a second optical system that condenses the light scattered from said semiconductor material;
   a polarization prism for separating said condensed light into a plurality of light rays in different light paths;
   a plurality of detectors for detecting said light rays that are separated in different light paths; and
   a computer for computing ratios between the detected intensities of a plurality of light signals;

wherein said first and second optical systems have optical axes thereof forming an angle of 50° to 120° relative to each other; and wherein said first and second optical systems have the optical axes thereof forming different angles relative to the normal to the surface of said semiconductor material.

16. An inspection method of discriminating a foreign particle on a semiconductor substrate and a defect in the semiconductor substrate, comprising the steps of:

irradiating the surface of said semiconductor substrate with light;

detecting said foreign particle by side scattered light of said light; and detecting said defect by backward scattered light of said light.

17. A method of manufacturing a semiconductor device, comprising the steps of:

placing a semiconductor wafer on a stage;

irradiating the surface of said semiconductor substrate with light;

detecting a particle on the surface of said semiconductor wafer by side scattered light of said light;

detecting said defect in said semiconductor wafer by backward scattered light of said light; and exposing said semiconductor wafer to heat treatment after the detection.

* * * * *

UNITED STATES PATENT AND TRADEMARK OFFICE
CERTIFICATE OF CORRECTION

PATENT NO : 5,936,726
DATED : August 10, 1999
INVENTOR(S) : Kazuo TAKEDA et al.

It is certified that error appears in the above-identified patent and that said Letters Patent is hereby corrected as shown below:

On title page, item 22 PCT Filed
replace "Mar. 10, 1996"
with --Mar. 10, 1995--.

Signed and Sealed this

Twenty-eighth Day of March, 2000

Attest:

Q. TODD DICKINSON

*Attesting Officer*     *Commissioner of Patents and Trademarks*